(12) United States Patent
Jung et al.

(10) Patent No.: US 11,779,254 B2
(45) Date of Patent: Oct. 10, 2023

(54) METHOD FOR PROCESSING BIOMETRIC SIGNAL AND ELECTRONIC DEVICE AND STORAGE MEDIUM FOR THE SAME

(71) Applicant: Samsung Electronics Co., Ltd., Suwon-si (KR)

(72) Inventors: Hyunjun Jung, Suwon-si (KR); Gunwoo Jin, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 395 days.

(21) Appl. No.: 16/950,201

(22) Filed: Nov. 17, 2020

(65) Prior Publication Data

US 2021/0177290 A1 Jun. 17, 2021

(30) Foreign Application Priority Data

Dec. 11, 2019 (KR) .......................... 10-2019-0164746

(51) Int. Cl.
*A61B 5/318* (2021.01)
*G06F 1/16* (2006.01)
(Continued)

(52) U.S. Cl.
CPC .............. *A61B 5/318* (2021.01); *A61B 5/681* (2013.01); *A61B 5/7225* (2013.01); *G06F 1/163* (2013.01); *G16H 40/67* (2018.01); *H03F 3/45* (2013.01)

(58) Field of Classification Search
CPC ....... A61B 5/318; A61B 5/681; A61B 5/7225; A61B 5/02416; A61B 5/282; A61B 5/276; A61B 5/332; A61B 5/6844; A61B 5/72; A61B 5/7445; G06F 1/163; G06F 1/1684; G06F 1/169; G06F 2203/0339;
(Continued)

(56) References Cited

U.S. PATENT DOCUMENTS

2006/0009691 A1 1/2006 Yeo et al.
2009/0024017 A1* 1/2009 Ruffini ...................... A61B 5/25
600/395
(Continued)

FOREIGN PATENT DOCUMENTS

JP           3849955 B2    11/2006
KR    10-1998-0000363 A    3/1998
(Continued)

OTHER PUBLICATIONS

International Search Report dated Feb. 18, 2021, issued in International Application No. PCT/KR2020/016157.

*Primary Examiner* — Brian T Gedeon
*Assistant Examiner* — Joshua Andrew Schum-Houck
(74) *Attorney, Agent, or Firm* — Jefferson IP Law, LLP

(57) ABSTRACT

A wearable electronic device is provided. The electronic device includes a plurality of electrodes configured to measure a biometric signal, an offset correction circuit, at least one processor operatively connected with the plurality of electrodes and the offset correction circuit, and a memory operatively connected with the at least one processor, wherein the memory stores instructions executed to enable the at least one processor to measure an offset between voltages via at least two electrodes among the plurality of electrodes and correct the offset via the offset correction circuit to allow the measured offset to fall within a threshold range.

18 Claims, 20 Drawing Sheets

(51) Int. Cl.
*A61B 5/00* (2006.01)
*H03F 3/45* (2006.01)
*G16H 40/67* (2018.01)

(58) Field of Classification Search
CPC .......... G16H 40/67; G16H 40/63; H03F 3/45; H03F 3/45475; H03F 3/45968; H03F 2203/45212
See application file for complete search history.

(56) References Cited

U.S. PATENT DOCUMENTS

| | | | |
|---|---|---|---|
| 2012/0265080 A1 | 10/2012 | Yu et al. | |
| 2013/0133397 A1 | 5/2013 | Kim et al. | |
| 2014/0316229 A1* | 10/2014 | Tognetti | A61B 5/0531 600/383 |
| 2016/0073914 A1* | 3/2016 | Lapetina | A61B 5/282 600/384 |
| 2019/0117100 A1* | 4/2019 | Rollie | A61B 5/0006 |
| 2021/0000376 A1 | 1/2021 | Lee et al. | |

FOREIGN PATENT DOCUMENTS

| | | |
|---|---|---|
| KR | 10-2005-0119890 A | 12/2005 |
| KR | 10-1298286 B1 | 8/2013 |
| KR | 10-2019-0097474 A | 8/2019 |
| KR | 10-2019-0098327 A | 8/2019 |
| WO | 2014/147024 A1 | 9/2014 |

\* cited by examiner

METHOD FOR PROCESSING BIOMETRIC SIGNAL AND ELECTRONIC DEVICE AND STORAGE MEDIUM FOR THE SAME

CROSS-REFERENCE TO RELATED APPLICATION(S)

This application is based on and claims priority under 35 U.S.C. § 119(a) of a Korean patent application number 10-2019-0164746, filed on Dec. 11, 2019, in the Korean Intellectual Property Office, the disclosure of which is incorporated by reference herein in its entirety.

BACKGROUND

1. Field

The disclosure relates to a method for processing biometric signals and an electronic device and storage medium for the same.

2. Description of Related Art

Recently, the use of portable electronic devices, such as smart phones, tablet personal computers (PCs), wearable electronic devices, or the like, is increasing, and as electronic technology is developed, a technology for measuring biometric signals is also developing. More particularly, technology for continuously measuring a user's biometric signals via an electronic device routinely worn by the user, such as a wearable electronic device, has been developed. The electronic device may include various sensors capable of detecting the user's biometric signals and provide various health-care functions via the sensors. For example, there may be various types of biometric signals, including electrical signals, such as electrocardiography (ECG) and electromyogram (EMG), physical signals, such as blood pressure, body temperature, and photoplethysmogram (PPG), and composition-related signals, such as blood glucose level, oxygen saturation, and body composition.

The above information is presented as background information only to assist with an understanding of the disclosure. No determination has been made, and no assertion is made, as to whether any of the above might be applicable as prior art with regard to the disclosure.

SUMMARY

Among the above-enumerated biometric signals, electrical signals, such as an electrocardiogram, are detected through electrodes in contact with the body skin. Therefore, in order to accurately and periodically measure the electrocardiogram, it may be critical to accurately place and attach the electrodes to the body. However, during periodic ECG measurement, the contact impedance between electrodes can be severely varied depending on the contact state of the electrodes contacting the body, and as a result, it may be unstable in obtaining biometric signals, deteriorating the accuracy and reliability in continuous ECG management.

Further, as a recent consumption trend places more importance on design, selection of materials for wearable electronic devices, as well as the external design of wearable electronic devices, is considered a critical factor in the development of wearable electronic devices.

However, when measuring a biometric signal, the contact impedance may vary depending on the user, the measurement environment, and the measurement time, as well as the size, material, and skin characteristics of the two electrodes. In addition, in the case of a wearable electronic device, the contact impedance may be relatively lowered by not only the wearing posture but also the wearing condition. For example, as the user's skin secretes sweat at an interface with the contacting material, the contact impedance may be relatively reduced. Accordingly, a change in contact impedance may occur due to various factors, such as the wearing state of the wearable electronic device and the measurement environment, which may also be a limitation in design development of the wearable electronic device.

Thus, a need exists for preventing deterioration of performance due to a change in contact impedance that occurs while wearing a wearable electronic device.

Aspects of the disclosure are to address at least the above-mentioned problems and/or disadvantages and to provide at least the advantages described below. Accordingly, an aspect of the disclosure is to provide an apparatus and a method for processing a biometric signal in a wearable electronic device is provided.

Additional aspects will be set forth in part in the description which follows and, in part, will be apparent from the description, or may be learned by practice of the presented embodiments.

In accordance with an aspect of the disclosure, a wearable electronic device is provided. The electronic device includes a plurality of electrodes configured to measure a biometric signal, an offset correction circuit, at least one processor operatively connected with the plurality of electrodes and the offset correction circuit, and a memory operatively connected with the at least one processor, wherein the memory stores instructions executed to enable the at least one processor to measure an offset between voltages via at least two electrodes among the plurality of electrodes and correct the offset via the offset correction circuit to allow the measured offset to fall within a threshold range.

In accordance with another aspect of the disclosure, a method for processing a biometric signal in a wearable electronic device is provided. The method includes measuring an offset between voltages via at least two electrodes among a plurality of electrodes for measuring the biometric signal in the wearable electronic device and correcting the offset to allow the measured offset to fall within a threshold range.

In accordance with another aspect of the disclosure a storage medium storing instructions is provided. The storage medium storing instructions are configured to be executed by at least one processor to enable the at least one processor to perform at least one operation, the at least one operation includes measuring an offset between voltages via at least two electrodes among a plurality of electrodes for measuring a biometric signal in a wearable electronic device and correcting the offset to allow the measured offset to fall within a threshold range.

Other aspects, advantages, and salient features of the disclosure will become apparent to those skilled in the art from the following detailed description, which, taken in conjunction with the annexed drawings, discloses various embodiments of the disclosure.

BRIEF DESCRIPTION OF THE DRAWINGS

The above and other aspects, features, and advantages of certain embodiments of the disclosure will be more apparent from the following description taken in conjunction with the accompanying drawings, in which.

Throughout the drawings, like reference numerals will be understood to refer to like parts, components, and structures.

DETAILED DESCRIPTION

The following description with reference to the accompanying drawings is provided to assist in a comprehensive understanding of various embodiments of the disclosure as defined by the claims and their equivalents. It includes various specific details to assist in that understanding but these are to be regarded as merely exemplary. Accordingly, those of ordinary skill in the art will recognize that various changes and modifications of the various embodiments described herein can be made without departing from the scope and spirit of the disclosure. In addition, descriptions of well-known functions and constructions may be omitted for clarity and conciseness.

The terms and words used in the following description and claims are not limited to the bibliographical meanings, but, are merely used by the inventor to enable a clear and consistent understanding of the disclosure. Accordingly, it should be apparent to those skilled in the art that the following description of various embodiments of the disclosure is provided for illustration purpose only and not for the purpose of limiting the disclosure as defined by the appended claims and their equivalents.

It is to be understood that the singular forms "a," "an," and "the" include plural referents unless the context clearly dictates otherwise. Thus, for example, reference to "a component surface" includes reference to one or more of such surfaces.

Hereinafter, various example embodiments of the disclosure will be disclosed with reference to the accompanying drawings.

The terms as used herein are provided merely to describe various example embodiments thereof, but not to limit the scope of other embodiments of the disclosure. It is to be understood that the singular forms "a", "an" and "the" include plural references unless the context clearly dictates otherwise. All terms including technical and scientific terms used herein have the same meaning as commonly understood by one of ordinary skill in the art to which the embodiments of the disclosure belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In some cases, the terms defined herein may be interpreted to exclude embodiments of the disclosure.

Figure 1A:
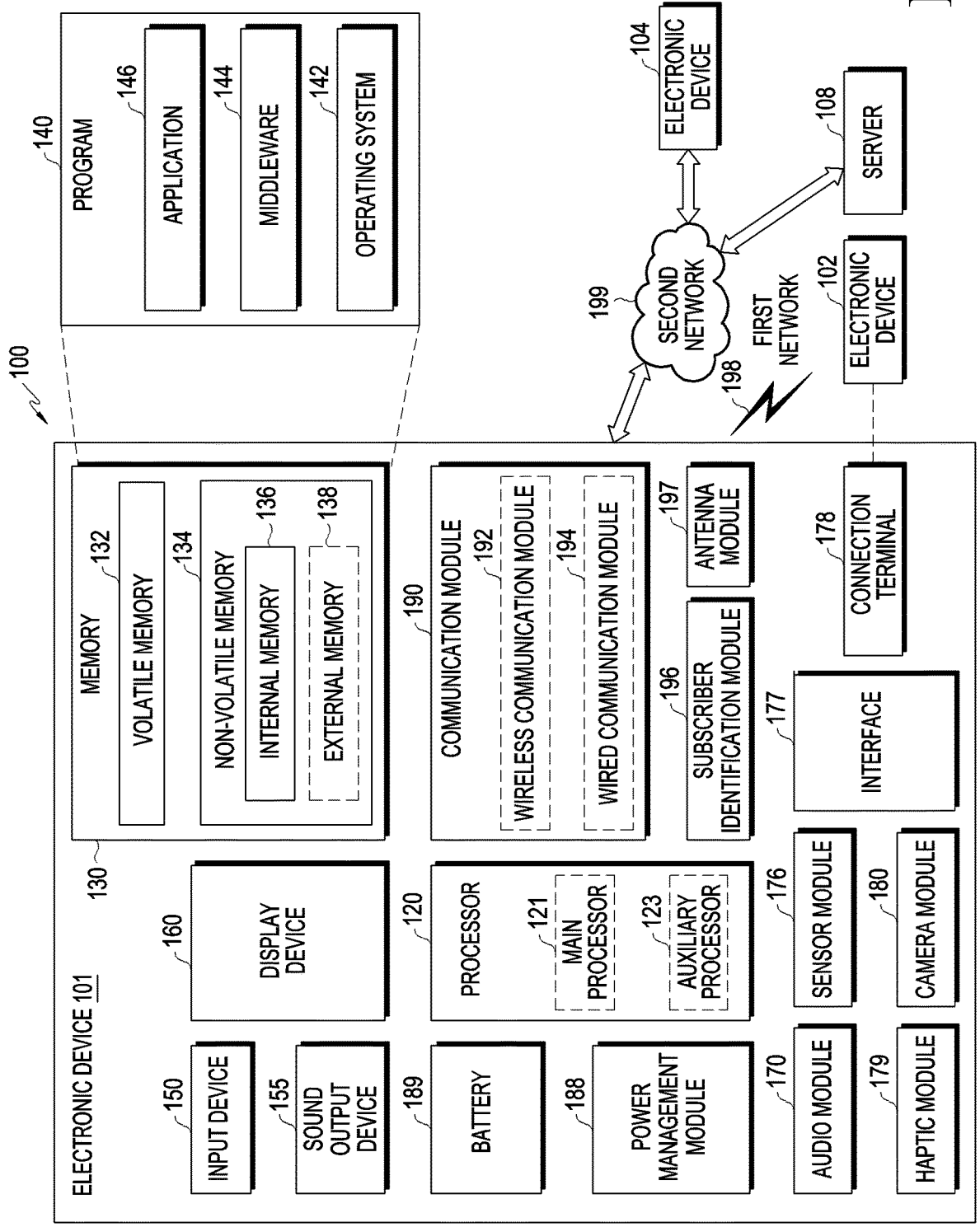
FIG. 1A is a block diagram illustrating an electronic device in a network environment according to an embodiment of the disclosure.

FIG. 1A is a block diagram illustrating an electronic device 101 in a network environment 100 according to an embodiment of the disclosure.

Referring to FIG. 1A, the electronic device 101 in the network environment 100a may communicate with an electronic device 102 via a first network 198 (e.g., a short-range wireless communication network), or an electronic device 104 or a server 108 via a second network 199 (e.g., a long-range wireless communication network). According to an embodiment of the disclosure, the electronic device 101 may communicate with the electronic device 104 via the server 108. According to an embodiment of the disclosure, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments of the disclosure, at least one (e.g., the display device 160 or the camera module 180) of the components may be omitted from the electronic device 101, or one or more other components may be added in the electronic device 101. In some embodiments of the disclosure, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to one embodiment of the disclosure, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment of the disclosure, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment of the disclosure, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input device 150 may receive a command or data to be used by other component (e.g., the processor 120) of the electronic device 101, from the outside (e.g., a user) of the electronic device 101. The input device 150 may include, for example, a microphone, a mouse, a keyboard, or a digital pen (e.g., a stylus pen).

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming calls. According to an embodiment of the disclosure, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment of the disclosure, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment of the disclosure, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment of the disclosure, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment of the disclosure, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment of the disclosure, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or motion) or electrical stimulus which may be recognized by a user via his tactile sensation or kinesthetic sensation. According to an embodiment of the disclosure, the haptic module 179 may include, for example, a motor, a piezoelectric element, or an electric stimulator.

The camera module 180 may capture a still image or moving images. According to an embodiment of the disclosure, the camera module 180 may include one or more lenses, image sensors, image signal processors, or flashes.

The power management module 188 may manage power supplied to the electronic device 101. According to one embodiment of the disclosure, the power management module 188 may be implemented as at least part of, for example, a power management integrated circuit (PMIC).

The battery 189 may supply power to at least one component of the electronic device 101. According to an embodiment of the disclosure, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment of the disclosure, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device). According to an embodiment of the disclosure, the antenna module may include one antenna including a radiator formed of a conductor or conductive pattern formed on a substrate (e.g., a printed circuit board (PCB)). According to an embodiment of the disclosure, the antenna module 197 may include a plurality of antennas. In this case, at least one antenna appropriate for a communication scheme used in a communication network, such as the first network 198 or the second network 199, may be selected from the plurality of antennas by, e.g., the communication module 190. The signal or the power may then be transmitted or received between the communication module 190 and the external electronic device via the selected at least one antenna. According to an embodiment of the disclosure, other parts (e.g., radio frequency integrated circuit (RFIC)) than the radiator may be further formed as part of the antenna module 197.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment of the disclosure, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment of the disclosure, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

Figure 1B:
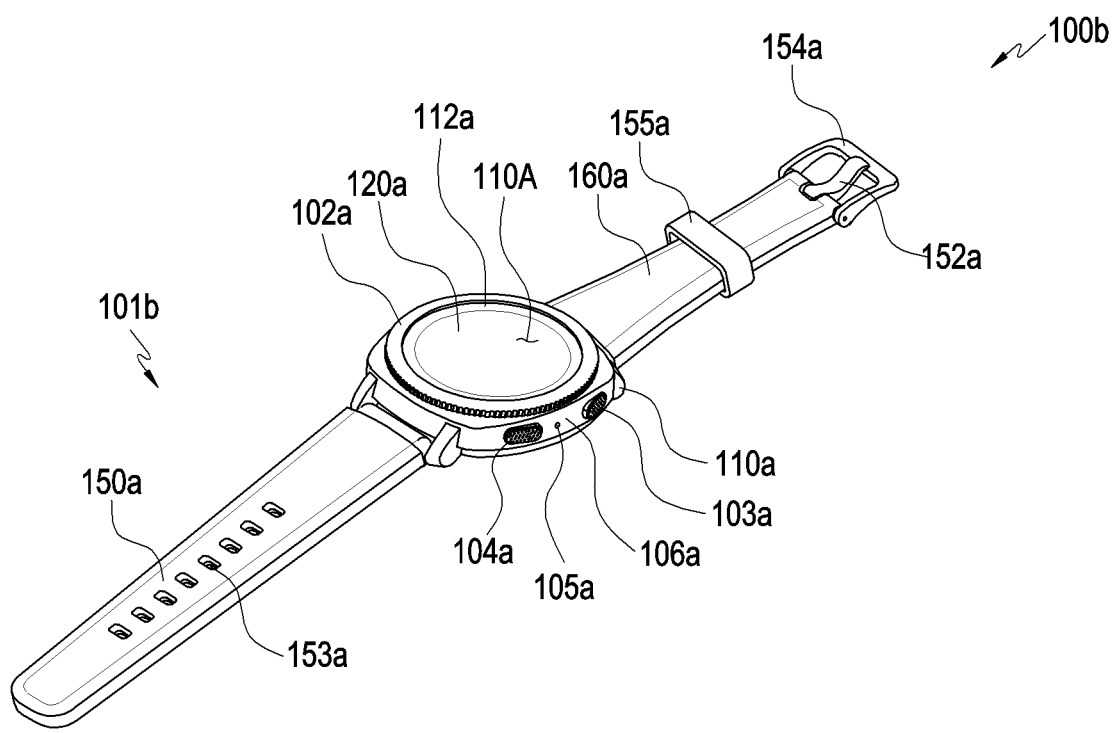
FIG. 1B is a front perspective view illustrating an electronic device according to an embodiment of the disclosure.

FIG. 1B is a front perspective view 100b illustrating an electronic device according to an embodiment of the disclosure.

Figure 1C:
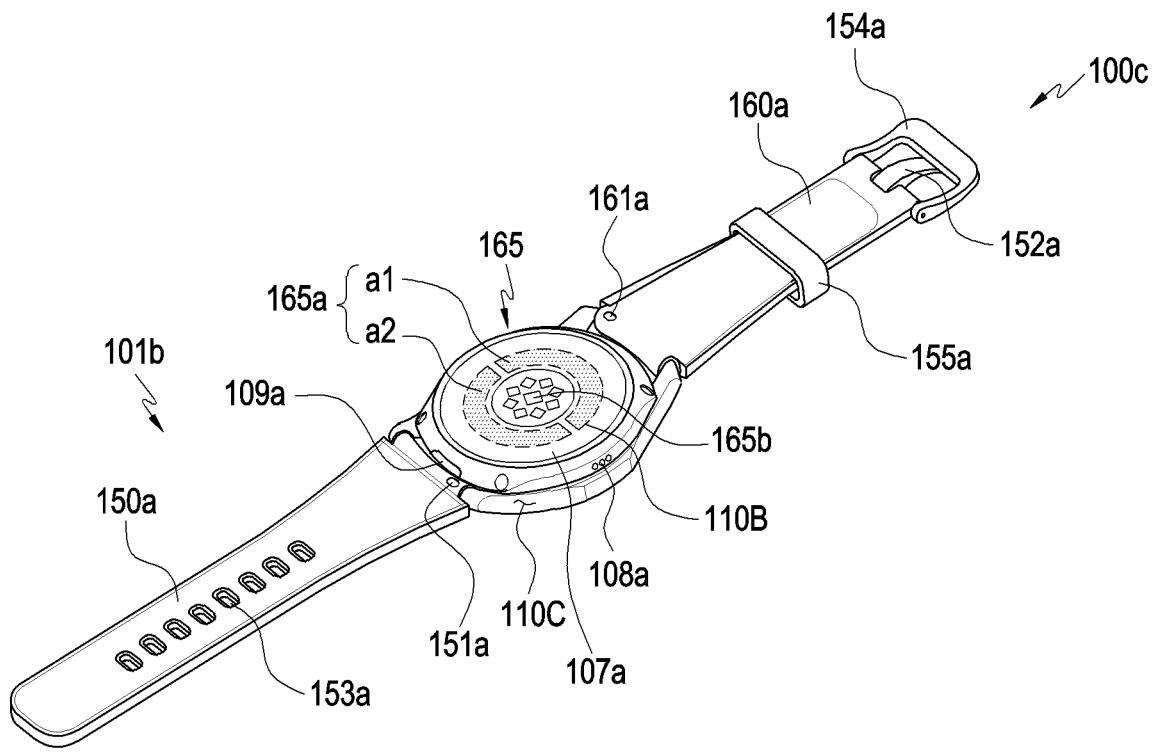
FIG. 1C is a rear perspective view illustrating an electronic device as shown in FIG. 1B according to an embodiment of the disclosure.

FIG. 1C is a rear perspective view 100c illustrating an electronic device as shown in FIG. 1B according to an embodiment of the disclosure.

Referring to FIGS. 1B and 1C, according to an embodiment of the disclosure, the wearable device 101b (e.g., the electronic device 101 of FIG. 1A) may include a housing 110a including a first surface (or front surface) 110A, a second surface (or rear surface) 110B, and a side surface 110C surrounding the space between the first surface 110A and the second surface 110B and coupling members 150a and 160a connected to at least part of the housing 110a and configured to allow the electronic device 101b to be detachably worn on the user's body portion (e.g., his wrist or ankle). According to another embodiment (not shown), the housing may denote a structure forming part of the first surface 110A, the second surface 110B, and the side surface 110C of FIGS. 1B and 1C. According to an embodiment of the disclosure, at least part of the first surface 110A may have a substantially transparent front plate 112a (e.g., a glass plate or polymer plate including various coat layers). The second surface 110B may be formed of a substantially opaque rear plate 107a. According to an embodiment of the disclosure, when the electronic device 101b includes a sensor module 165 disposed on the second surface 110B, the rear plate 107a may at least partially include a transparent region.

The rear plate 107a may be formed of, e.g., laminated or colored glass, ceramic, polymer, metal (e.g., aluminum, stainless steel (STS), or magnesium), or a combination of at least two thereof. The side surface 110C may be formed by a side bezel structure (or a "side member") 106a that couples to the front plate 112a and the rear plate 107a and includes a metal and/or polymer. According to an embodiment of the disclosure, the rear plate 107a and the side bezel structure 106a may be integrally formed together and include the same material (e.g., a metal, such as aluminum). The coupling members 150a and 160a may be formed of various materials in various shapes. A uni-body structure or multiple unit links which is flexible may be formed of fabric, leather, rubber, urethane, metal, ceramic, or a combination of at least two thereof.

According to an embodiment of the disclosure, the electronic device 101b may include at least one or more of a display 120a (refer to FIG. 1D), audio modules 105a and 108a, a sensor module 165, key input devices 102a, 103a, and 104a, and a connector hole 109a. According to an embodiment of the disclosure, the electronic device 101b may exclude at least one (e.g., the key input devices 102a, 103a, and 104a, connector hole 109a, or sensor module 165) of the components or may add other components.

According to an embodiment of the disclosure, the electronic device 101b may include a plurality of electrodes for measuring a biometric signal. At least one of the plurality of electrodes may be placed in at least one of the position of the key input device 102a, 103a, or 104a, the position of the bezel 106a, or the position of the display 120a or the housing 110a. Among the key input devices, the wheel key 102a may include a rotary bezel.

The display 120a may be exposed through a substantial portion of, e.g., the front plate 112a. The display 120a may have a shape corresponding to the shape of the front plate 112a, e.g., a circle, ellipse, or polygon. The display 120a may be coupled with, or disposed adjacent, a touch detection circuit, a pressure sensor capable of measuring the strength (pressure) of touches, and/or fingerprint sensor.

According to an embodiment of the disclosure, the display 120a may include at least one transparent electrode for measuring biometric signals among the plurality of electrodes for measuring biometric signals.

The audio modules 105a and 108a may include a microphone hole 105a and a speaker hole 108a. The microphone hole 105a may have a microphone inside to obtain external sounds. According to an embodiment of the disclosure, there may be a plurality of microphones to be able to detect the direction of a sound. The speaker hole 108a may be used for an external speaker or a receiver for phone talks. According to an embodiment of the disclosure, a speaker may be included without the speaker hole (e.g., a piezo speaker).

The sensor module 165 may generate an electrical signal or data value corresponding to an internal operating state or external environmental state of the electronic device 101b. The sensor module 165, e.g., a biometric sensor module 165 (e.g., an HRM sensor) placed on the second surface 110B of the housing 110a, may include an electrocardiogram (ECG) sensor 165a including at least two electrodes a1 and a2 for ECG measurement and a photoplethysmogram (PPG) sensor 165b for heartrate measurement. The electronic device 101b may further include sensor modules not shown, e.g., at least one of a gesture sensor, a gyro sensor, an atmospheric pressure sensor, a magnetic sensor, an acceleration sensor, a grip sensor, a color sensor, an infrared (IR) sensor, a biometric sensor, a temperature sensor, a humidity sensor, or an illuminance sensor.

The key input devices 102a, 103a, and 104a may include a wheel key 102a disposed on the first surface 110A of the housing 110a to be rotatable in at least one direction and/or side key buttons 103a and 104a disposed on the side surface 110C of the housing 110a. The wheel key 102a may have a shape corresponding to the shape of the front plate 112a. According to an embodiment of the disclosure, the electronic device 101b may exclude all or some of the above-mentioned key input devices 102a, 103a, and 104a and the excluded key input devices 102a, 103a, and 104a may be implemented in other forms, e.g., as soft keys on the display 120a. The connector hole 109a may receive a connector (e.g., a universal serial bus (USB) connector) for transmitting and receiving power and/or data to/from an external electronic device. Another connector hole (not shown) may be included for receiving a connector for transmitting and receiving audio signals to/from the external electronic device. The electronic device 101b may further include a connector cover (not shown) to cover at least part of, e.g., the connector hole 109a and preventing undesirable materials from entering the connector hole.

The coupling members 150a and 160a may detachably be fastened to at least portions of the housing 110a via locking members 151a and 161a. The locking members 151a and 161a may include components or parts for coupling, such as pogo pins, and, according to an embodiment of the disclosure, may be replaced with protrusions or recesses formed on/in the coupling members 150a and 160a. For example, the coupling members 150a and 160a may be coupled in such a manner as to be fitted into or over the recesses or protrusions formed on the housing 110a. The coupling members 150a and 160a may include one or more of a fastening member 152a, fastening member coupling holes 153a, a band guide member 154a, and a band fastening ring 155a.

The fastening member 152a may be configured to allow the housing 110a and the coupling members 150a and 160a to be fastened to the user's body portion (e.g., wrist or ankle). The fastening member coupling holes 153a may fasten the housing 110a and the coupling members 150a and 160a to the user's body portion, corresponding to the fastening member 152a. The band guide member 154a may be configured to restrict movement of the fastening member 152a to a certain range when the fastening member 152a fits into one of the fastening member coupling holes 153a, thereby allowing the coupling members 150a and 160a to be tightly fastened onto the user's body portion. The band fastening ring 155a may limit the range of movement of the coupling members 150a and 160a, with the fastening member 152a fitted into one of the fastening member coupling holes 153a.

Figure 1D:
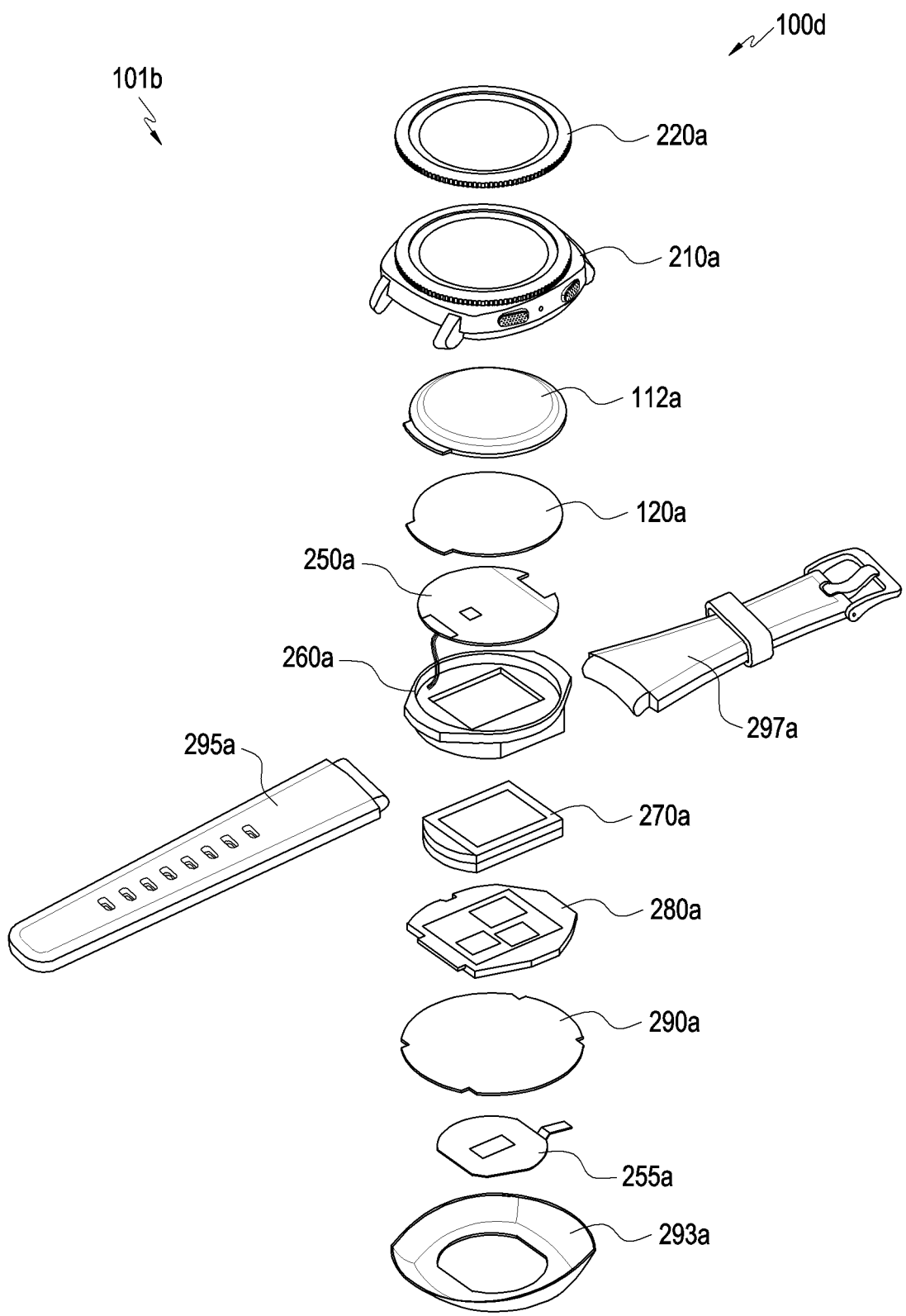
FIG. 1D is an exploded perspective view illustrating an electronic device as shown in FIG. 1B according to an embodiment of the disclosure.

FIG. 1D is an exploded perspective view 100c illustrating an electronic device 101b of FIG. 1B according to an embodiment of the disclosure.

Referring to FIG. 1D, an electronic device 101b (e.g., the electronic device 101 of FIG. 1A) may include a side bezel structure 210a, a wheel key 220a, a front plate 112a, a display 120a, a first antenna 250a, a second antenna 255a, a supporting member 260a (e.g., a bracket), a battery 270a, a printed circuit board 280a, a sealing member 290a, a rear plate 293a, and coupling members 295a and 297a. At least one of the components of the electronic device 101b may be the same or similar to at least one of the components of the electronic device 101b of FIG. 1A or 1C and no duplicate description is made below. The supporting member 260a may be disposed inside the electronic device 101b to be connected with the side bezel structure 210a or integrated with the side bezel structure 210a. The supporting member 260a may be formed of, e.g., a metal and/or non-metallic material (e.g., polymer). The display 120a may be joined onto one surface of the supporting member 260a, and the printed circuit board 280a may be joined onto the opposite surface of the supporting member 260a. A processor, memory, and/or interface may be mounted on the printed circuit board 280a. The processor may include one or more of, e.g., a central processing unit, an application processor, a graphic processing unit (GPU), a sensor processor, or a communication processor.

The memory may include, e.g., a volatile or non-volatile memory. The interface may include, e.g., a high definition multimedia interface (HDMI), a universal serial bus (USB) interface, a secure digital (SD) card interface, and/or an audio interface. The interface may electrically or physically connect, e.g., the electronic device 101b with an external electronic device and may include a USB connector, an SD card/multimedia card (MMC) connector, or an audio connector.

The battery 270a may be a device for supplying power to at least one component of the electronic device 101b. The battery 270a may include, e.g., a primary cell which is not rechargeable, a secondary cell which is rechargeable, or a fuel cell. At least a portion of the battery 270a may be disposed on substantially the same plane as the printed circuit board 280a. The battery 270a may be integrally or detachably disposed inside the electronic device 101b.

The first antenna 250a may be disposed between the display 120a and the supporting member 260a. The first antenna 250a may include an antenna, e.g., a near-field communication (NFC) antenna, a wireless charging antenna, and/or a magnetic secure transmission (MST) antenna. The first antenna 250a may perform short-range communication with an external device, wirelessly transmit/receive power necessary for charging, or transmit magnetic-based signals including payment data or short-range communication signals. According to an embodiment of the disclosure, an antenna structure may be formed by a portion or combination of the side bezel structure 210a and/or the supporting member 260a.

The second circuit board 255a may be disposed between the circuit board 280a and the rear plate 293a. The second circuit board 255a may include an antenna, e.g., a near-field communication (NFC) antenna, a wireless charging antenna, and/or a magnetic secure transmission (MST) antenna. The second circuit board 255a may perform short-range communication with an external device, wirelessly transmit/receive power necessary for charging, or transmit magnetic-based signals including payment data or short-range communication signals. According to an embodiment of the disclosure, an antenna structure may be formed by a portion or combination of the side bezel structure 210a and/or the rear plate 293a. According to an embodiment of the disclosure, when the electronic device 101b (e.g., the electronic device 101b of FIG. 1B or 1C) includes a sensor module (e.g., the sensor module 165 of FIG. 1B), a sensor element (e.g., a photoelectric conversion element or electrode pad) separate from the second circuit board 255a or the sensor circuit disposed on the second circuit board 255a may be disposed. For example, an electronic component provided as the sensor module 165 may be disposed between the circuit board 280a and the rear plate 293a.

The sealing member 290a may be positioned between the side bezel structure 210a and the rear plate 293a. The sealing member 290a may be configured to block moisture or foreign bodies that may enter the space surrounded by the side bezel structure 210a and the rear plate 293a, from the outside.

According to an embodiment of the disclosure, examples of measurable biometric signals may include electrical signals, such as electrocardiogram (ECG), electroencephalography (EEG), and electromyography (EMG), physical signals, such as blood pressure, body temperature, and PPG, and composition-related signals, such as blood glucose level, oxygen saturation, and body composition. However, the measurable biometric signals are not limited thereto. Although the following description focuses primarily on examples of correcting a DC offset for ECG signals, this is merely for illustration purposes, and embodiments are not limited thereto.

The electrocardiogram is an electrical signal generated by the heartbeat and may be obtained by measuring the difference in voltage between electrodes using electrodes in different positions of the human body, that is, two different biological positions. Measuring such an electrocardiogram may detect irregularities in the heartbeat and thus diagnose heart-related signs, such as arrhythmia and heart artery disease. Such an electrocardiogram is an electrical alternating current (AC) signal measured by two parts of a living body, and because it has a very small signal level (e.g., 1 mV or less), an amplification circuit may be required. In order to completely measure the AC component in a system using a unipolar power source among systems for measuring the same, such a method of applying a bias voltage using a third electrode, as well as the measurement electrode, may be primarily used. To this end, a measurement system using a high-resolution analog-to-digital conversion circuit (ADC) may obtain an electrocardiogram signal that may be sufficiently analyzed even with low gain amplification due to an increase in resolution.

Various types of analog front ends (AFEs) may be used to measure the user's biometric signal in the wearable electronic device. In this case, in relation to healthcare, wearable electronic devices operate with batteries, and most of them use a unipolar voltage as a supply voltage, so that AFE providers are designing AFE devices to operate with a single power supply. AFEs for this purpose may be operated in such a manner as to apply a direct current (DC) bias to obtain an AC-type biometric signal. However, there may be a difference between the DC values at the two electrodes applied to the input of the differential amplifier, and due to this, measurement may be difficult outside the input dynamic range (or operation range) of the ADC. For example, a significant difference in DC voltage may arise due to a mismatch in contact impedance in different input paths (e.g., P or N) through the electrodes. Accordingly, if the DC values at these two electrodes are corrected to fall within the input dynamic range, ECG information in a wider bandwidth including DC may be provided. In addition, the low-gain, high-resolution measurement system as described above may perform faster measurement than previous measurement systems due to the structure that does not require a high-pass filter.

According to an embodiment of the disclosure, a device for processing biometric signals may be implemented in the form of a low-gain, high-resolution measurement system.

According to an embodiment of the disclosure, a device for processing biometric signals may be a wearable electronic device. The wearable electronic device may include a housing and/or a bezel. The rear surface of the housing, i.e., the rear surface of the wearable electronic device, may contact a body portion (e.g., wrist), and the rear surface may be formed of metal. According to an embodiment of the disclosure, electrodes for measuring biometric signals may be arranged around the center portion of the rear surface. The arrangement of the electrodes is described below with reference to FIG. 4A.

A biometric signal processing device implemented in the form of a low-gain, high-resolution measurement system may measure biometric signals using dry electrodes. Such a dry electrode exhibits a high contact resistance at the initial stage of contact and, as the contact area reduces, the variation in contact impedance may increase. The contact impedance may vary depending on users, measurement environments, and measurement times and, in particular, the contact impedance may be altered by the size of the two electrodes and the material.

Figure 2:
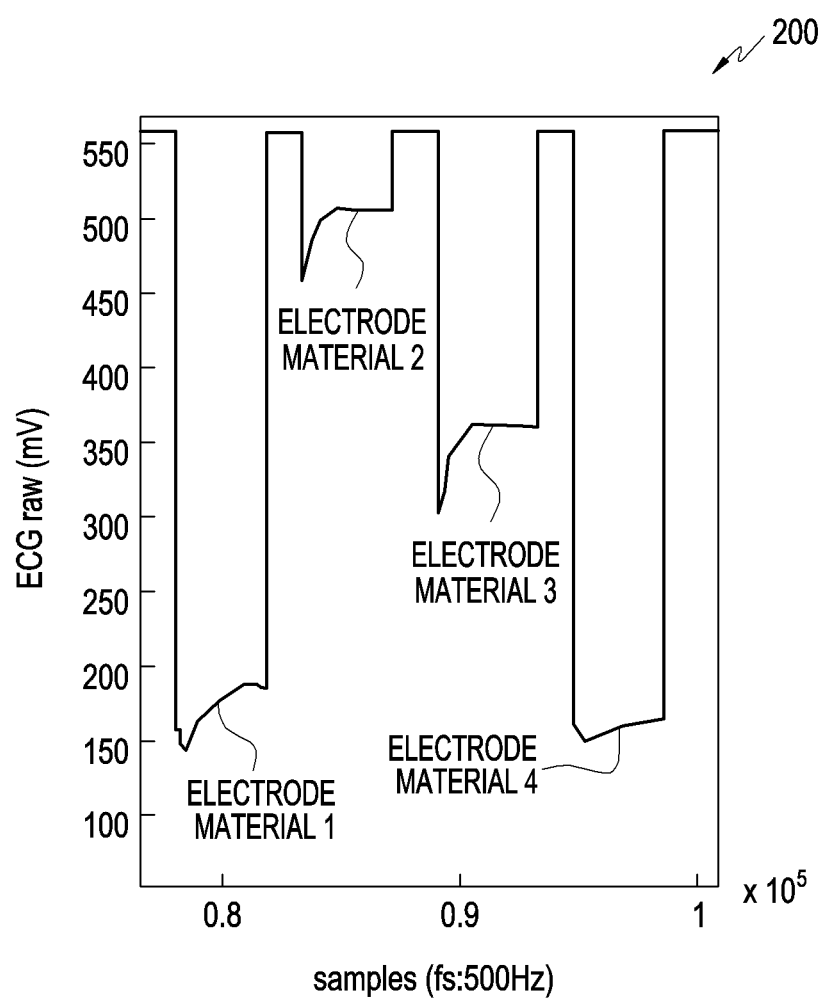
FIG. 2 is a graph illustrating direct current (DC) offset differences depending on electrode materials, according to an embodiment of the disclosure.

FIG. 2 is a graph 200 illustrating DC offset differences depending on electrode materials according to an embodiment of the disclosure.

Referring to FIG. 2, ECG raw data obtained via dry electrodes formed of different electrode materials. In FIG. 2, the vertical axis denotes the ECG raw data, and the horizontal axis denotes the time. FIG. 2 shows that the DC offset may be varied depending on electrode materials. It may be identified from FIG. 2 that the ECG raw data differs for each of different electrode materials, e.g., electrode materials 1 to 4. According to an embodiment of the disclosure, characteristics that cause a difference in DC offset may include characteristics according to a coating of the electrode, the color of the electrode, characteristics according to printing, and an operation difference for each device, as well as the material of the electrode. For example, various materials may be used for the electrodes, such as stainless steel (STS, SUS, or the like), aluminum, titanium, ceramic, and chromium.

For example, a different DC offset may be exhibited for each electrode material. For electrode material 1, the DC offset may be about 150 mV and, for electrode material 2, the DC offset may be about 500 mV. As such, depending on the electrode materials, the difference in DC offset may increase and the chance of obtaining signals off the normal range may increase. Further, for example, even when the color of the electrode is changed, e.g., silver or rose gold, the DC offset may be varied. Depending on what colors are used for the electrodes, the difference in DC offset between the electrodes may significantly increase. For example, as in the case of electrode material 2, if the DC offset (e.g., about 500 mV) of electrode material 2 approaches the upper limit threshold (e.g., 550 mV) of the input dynamic range (or operation range) of the analog-to-digital converter (ADC) due to the difference (e.g., DC voltage) between the two electrodes, it may be unstable to obtain a biometric signal. Similarly, even when the DC offset approaches the lower limit threshold of the input operation range, obtaining a biometric signal may be unstable. Here, the input dynamic range may include the upper limit threshold and the lower limit threshold. According to an embodiment of the disclosure, the input dynamic range may have a predetermined range, e.g., a range from about 0 mV to about 550 mV.

If the DC offset departs from the input dynamic range, i.e., when the signal has an amplitude larger than the input dynamic range, saturation may occur, causing it difficult to obtain a biometric signal. In the case of expanding the input dynamic range, noise signals may be received, so that the signal-to-noise ratio (SNR) may be lowered. Thus, a correction may need to be performed to allow the DC offset to fall within the input dynamic range.

According to an embodiment of the disclosure, an offset correction circuit capable of correcting the DC difference between the two electrodes in the biometric signal processing device implemented in the form of a low-gain, high-resolution measurement system, may be added. Thus, it may operate robust despite a mismatch in contact impedance. By so doing, a differentially amplified DC-type biometric signal (e.g., ECG raw data) may be rendered to fall within the input dynamic range, so that it is possible to obtain a stable biometric signal regardless of the difference between the two electrodes due to various measurement environments, as well as the material of the electrodes.

A method for processing biometric signals and embodiments of a wearable electronic device are described below with reference to the drawings.

Figure 3:
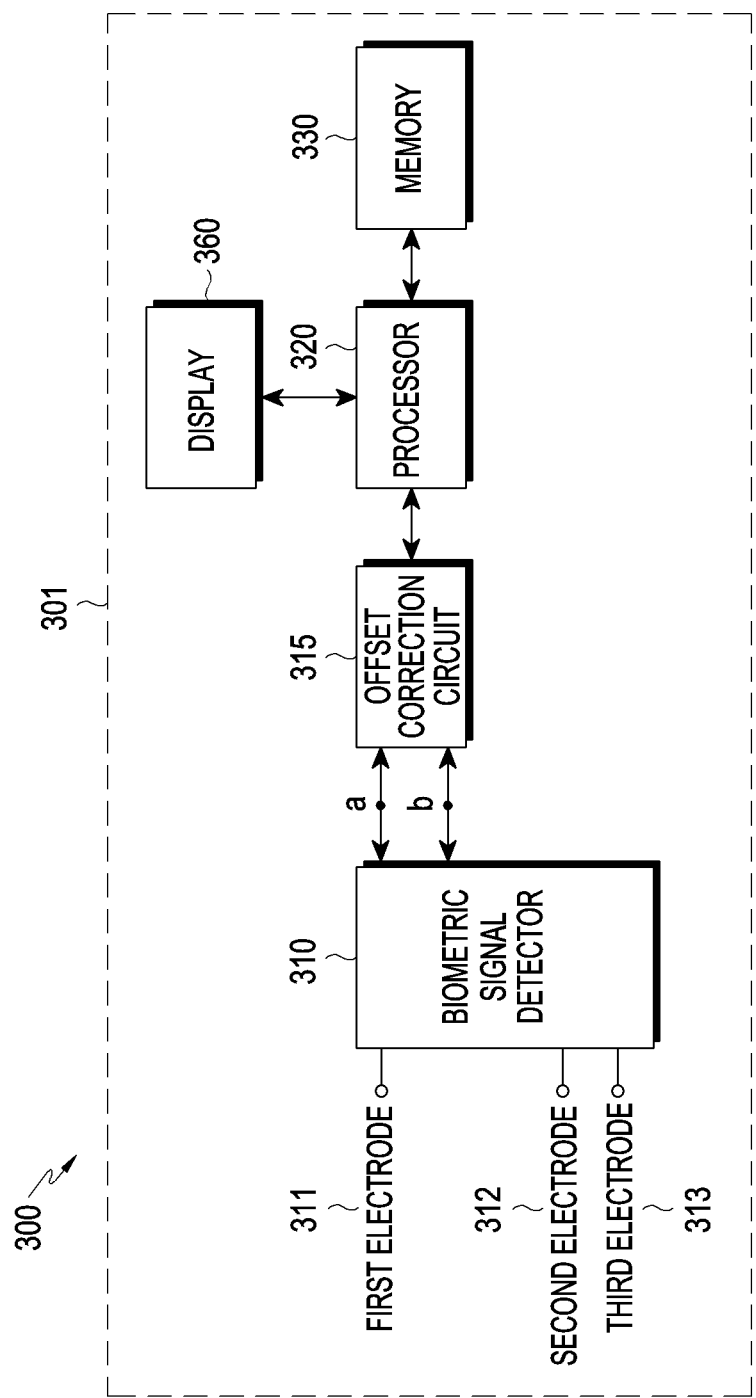
FIG. 3 is a block diagram schematically illustrating a biometric signal processing device according to an embodiment of the disclosure.

FIG. 3 is a block diagram 300 schematically illustrating a biometric signal processing device according to an embodiment of the disclosure.

FIG. 3 is a block diagram illustrating an internal configuration of a biometric signal processing device according to an embodiment. The biometric signal processing device may be a wearable electronic device. According to an embodiment of the disclosure, the biometric signal processing device may be equipped, in the form of a hardware or software module, in an electronic device, such as a wearable electronic device. The biometric signal processing device may be implemented as a stand-alone hardware device in which case it may be used to obtain and analyze various kinds of biometric signals. However, without limitations thereto, various modifications may be made thereto depending on the purposes of utilizing the instant technology.

Referring to FIG. 3, a biometric signal processing device 301 may include a biometric signal detector 310, an offset correction circuit 315, a processor 320, a memory 330, and a display 360. Here, the biometric signal processing device 301 may be a wearable electronic device (e.g., the electronic device 101 of FIG. 1A).

The biometric signal detector 310 may receive a signal for obtaining biometric signals having different electrical physical quantities from a plurality of electrodes 311, 312, and 313. The plurality of electrodes may be a plurality of sensors. The plurality of sensors may include various sensors, including an ECG sensor, a heartrate measurement sensor, a body temperature measurement sensor, or a bio-impedance measurement sensor.

According to an embodiment of the disclosure, the biometric signal detector 310 may include a biometric sensor including the plurality of electrodes 311, 312, and 313 for measuring biometric signals, and the plurality of electrodes 311, 312, and 313 may include a first electrode 311, a second electrode 312, and a third electrode 313. For example, an ECG signal indicating the electrical activity of the user's heart may be detected via the first electrode 311, the second electrode 312, and the third electrode 313. The signals output via the electrodes may be electrical signals, and the electrical physical quantity of the output electrical signal may be the voltage.

The biometric signal detector 310 may receive signals detected via the plurality of electrodes 311, 312, and 313 and, according to an embodiment of the disclosure, the biometric signal detector 310 may include the plurality of electrodes 311, 312, and 313.

The offset correction circuit 315 may process signals for obtaining a biometric signal according to the electrical physical quantity, e.g., voltage, of the signals output from the biometric signal detector 310 and correct a DC offset between two signals to allow the DC offset to fall within a threshold range.

According to an embodiment of the disclosure, the offset correction circuit 315 may include buffers individually connected to the output terminals of the first electrode 311 and the third electrode 313, low pass filters individually connected to the output terminals of the buffers, and current sources individually connected to the low pass filters. According to an embodiment of the disclosure, the control capability for offset correction is determined by the resistance R (known) of the low pass filter and the applied current, e.g., the magnitude (I) (known) of the current. Since the resistance R is a fixed value, and the magnitude I of the current to be applied may be previously known, the offset correction may be performed linearly. As such, offset adjustment may be performed in proportion, corresponding to the magnitude I of the current of the current source and the fixed resistance via a circuit including buffers and low pass filters. This is described below with reference to FIG. 13.

Figure 11A:
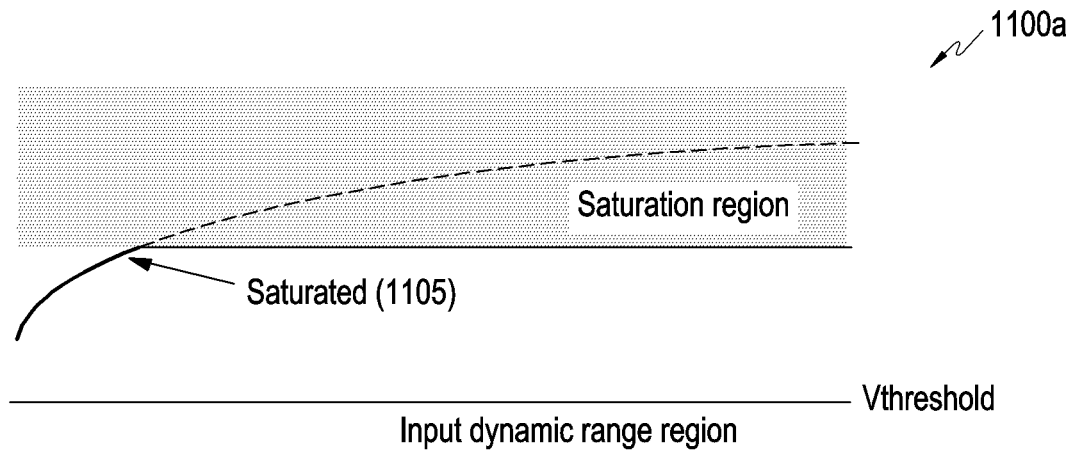
FIG. 11A is a view illustrating a signal upon offset non-correction according to an embodiment of the disclosure.

According to an embodiment of the disclosure, the offset correction circuit 315 may be implemented without buffers individually connected to the output terminals of the first electrode 311 and the third electrode 313 and low pass filters individually connected to the output terminals of the buffers. In other words, the offset correction circuit 315 may include a first electrode 311 and a third electrode 313 and a current source for each of the first electrode 311 and the third electrode 313. In this case, a current flows through the contact resistance (unknown) of the interface between the electrode and the skin. Since the contact resistance is a value varied during the measurement, offset correction may be performed non-linearly. Such offset adjustment may be adjusted non-linearly in a manner as shown in FIGS. 11A and 11C, and this is described below with reference to FIGS. 11A and 11C. The display 360 may display a user interface based on the biometric signal measured upon executing an application for biometric signal measurement (e.g., an ECG application or a health-care application). The display 360 may output a guide screen or abnormal state upon measuring a biometric signal under the control of the processor 320.

According to an embodiment of the disclosure, a wearable electronic device comprises a plurality of electrodes configured to measure a biometric signal, an offset correction circuit, at least one processor 320 operatively connected with the plurality of electrodes and the offset correction circuit, and a memory 330 operatively connected with the at least one processor. The memory 330 may store instructions executed to enable the at least one processor to measure an offset between voltages via at least two electrodes among the plurality of electrodes and correct the offset via the offset correction circuit to allow the measured offset to fall within a threshold range.

According to an embodiment of the disclosure, the instructions may enable the at least one processor 320 to measure an offset between a first voltage via a first electrode among the at least two electrodes and a second voltage via a third electrode, with respect to a reference voltage, as the reference voltage is applied via a second electrode among the plurality of electrodes.

According to an embodiment of the disclosure, the offset correction circuit (e.g., 550 of FIG. 5B) may include a first current source between an output terminal of the first electrode and an input terminal of a differential amplifier and a second current source between an output terminal of the third electrode and an input terminal of the differential amplifier. According to an embodiment of the disclosure, the instructions may enable the at least one processor to measure the offset between the first voltage output from the first electrode and the second voltage output from the third electrode using the differential amplifier and, when the measured offset falls out of the threshold range, correct the offset by adjusting a current magnitude of any one of the first current source and the second current source for a voltage for the first electrode and a voltage for the third electrode.

According to an embodiment of the disclosure, the offset correction circuit (e.g., 550 of FIG. 5A) may include a first low pass filter receiving the first voltage output from the first electrode via a buffer, a second low pass filter receiving the second voltage output from the third electrode via a buffer, a first current source between an output terminal of the first low pass filter and an input terminal of a differential amplifier, and a second current source between an output terminal of the second low pass filter and the input terminal of the differential amplifier.

According to an embodiment of the disclosure, the instructions may enable the at least one processor 320 to measure the offset between the first voltage and the second voltage using the differential amplifier and, when the measured offset falls out of the threshold range, correct the offset via the offset correction circuit.

According to an embodiment of the disclosure, the instructions may enable the at least one processor 320 to, when the measured offset falls out of the threshold range, correct the offset by adjusting a current magnitude of any one of the first current source and the second current source for a voltage for the first electrode and a voltage for the third electrode.

According to an embodiment of the disclosure, the instructions may enable the at least one processor 320 to, when the measured offset is larger than an upper limit threshold of the threshold range, apply a second current of the second current source in a direction towards the third electrode to increase the voltage for the third electrode and decrease the voltage for the first electrode.

According to an embodiment of the disclosure, a voltage applied to the input terminal of the differential amplifier may be a sum of the voltage for the third electrode and a voltage resultant from multiplying a resistance of the second low pass filter by the second current of the second current source.

According to an embodiment of the disclosure, the instructions may enable the at least one processor 320 to adjust the offset to a magnitude corresponding to the voltage resultant from multiplying the resistance of the second low pass filter by the second current of the second current source.

According to an embodiment of the disclosure, the instructions may enable the at least one processor 320 to, when the measured offset is smaller than a lower limit threshold of the threshold range, apply a first current of the first current source in a direction towards the first electrode to decrease the voltage for the third electrode and increase the voltage for the first electrode.

According to an embodiment of the disclosure, a voltage applied to the input terminal of the differential amplifier may be a sum of the voltage for the first electrode and a voltage resultant from multiplying a resistance of the first low pass filter by the first current of the first current source.

According to an embodiment of the disclosure, the instructions may enable the at least one processor 320 to adjust the offset to a magnitude corresponding to the voltage resultant from multiplying the resistance of the first low pass filter by the first current of the first current source.

Figure 4A:
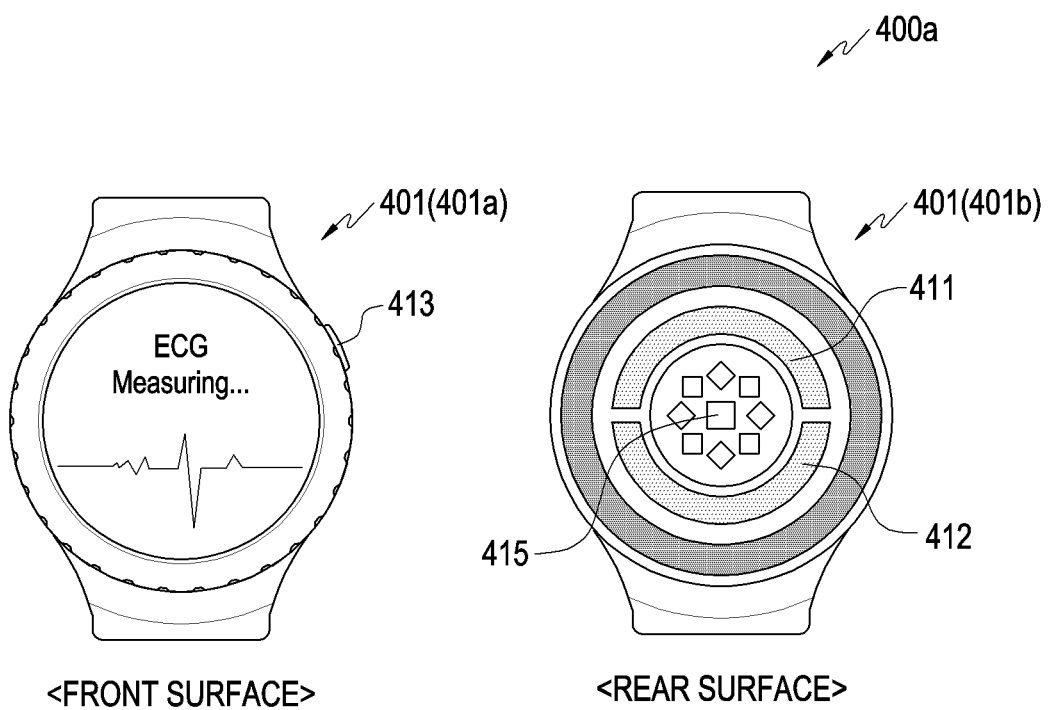
FIG. 4A is a view illustrating an arrangement of electrodes of a wearable electronic device according to an embodiment of the disclosure.

FIG. 4A is a view 400a illustrating an arrangement of electrodes of a wearable electronic device according to an embodiment of the disclosure.

Figure 4B:
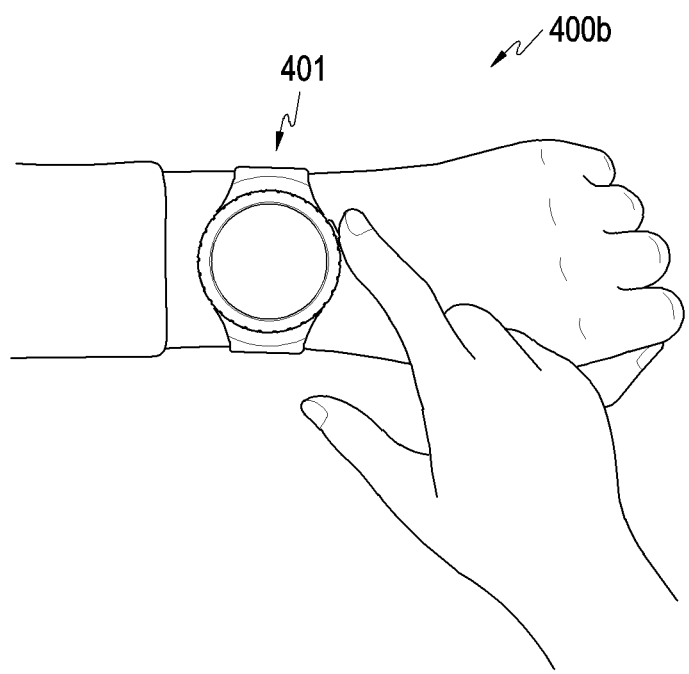
FIG. 4B is a view illustrating a method for measuring a biometric signal in a wearable electronic device according to an embodiment of the disclosure.

FIG. 4B is a view 400b illustrating a method for measuring a biometric signal in a wearable electronic device according to an embodiment of the disclosure.

FIG. 4A illustrates the front and rear surface of a wearable electronic device 401.

Referring to FIG. 4A, a first electrode 411 (e.g., the first electrode 311 of FIG. 3) for measuring biometric signals may be disposed on the rear surface 401b of the wearable electronic device 401, and a second electrode 412 (e.g., the second electrode 312 of FIG. 3) for applying voltage to the first electrode 411 and a third electrode 413 (e.g., the third electrode 313 of FIG. 3) may be disposed on the same surface as the first electrode 411. The third electrode 413 for measuring biometric signals may be disposed on a side surface of the wearable electronic device 401 which may be contacted by the other hand of the user than the hand holding the wearable electronic device 401.

For example, lead refers to a voltage difference between two electrodes being shown as an ECG signal and may be divided into a first lead Lead I, a second lead Lead II, and a third lead Lead III depending on measurement positions and the shape of the ECG signal may differ. Specifically, in the case of a band- or watch-type wearable electronic device 401 for measuring ECG, measurement is performed, with the wearable electronic device 401 placed on the user's wrist, so that a first lead of ECG signal which is a signal obtained from the right side of the heart to left side or from the left side of the heart to the right side may be obtained. For example, in the case of the wearable electronic device 401, if the left wrist is a positive (+) pole, a finger of the right hand is a negative (−) pole, and measuring the conductivity of the heart therebetween may be measuring the ECG signal.

Although FIG. 4A illustrates an example in which the second electrode 412 is disposed on the same surface (e.g., the rear surface) as the first electrode 411, and the third electrode 413 is disposed on a side surface of the wearable electronic device 401, the arrangement is not limited thereto. For example, one side surface between the front and rear surface of the wearable electronic device 401, e.g., a portion (e.g., edge) of the housing of the wearable electronic device 401 or the entire edge of the housing may be formed of the same material (e.g., metal), and any one of the portion of the edge or the entire edge formed of the same material may be used as the third electrode 413.

Referring to FIG. 4B, the wearable electronic device 401 may be worn on the user's wrist, and a first portion (e.g., the user's wrist) of the user's body may come in contact with the first electrode 411 and the second electrode 412, and a second portion (e.g., the user's finger) of the user's body may come in contact with the third electrode 413.

Figure 5A:
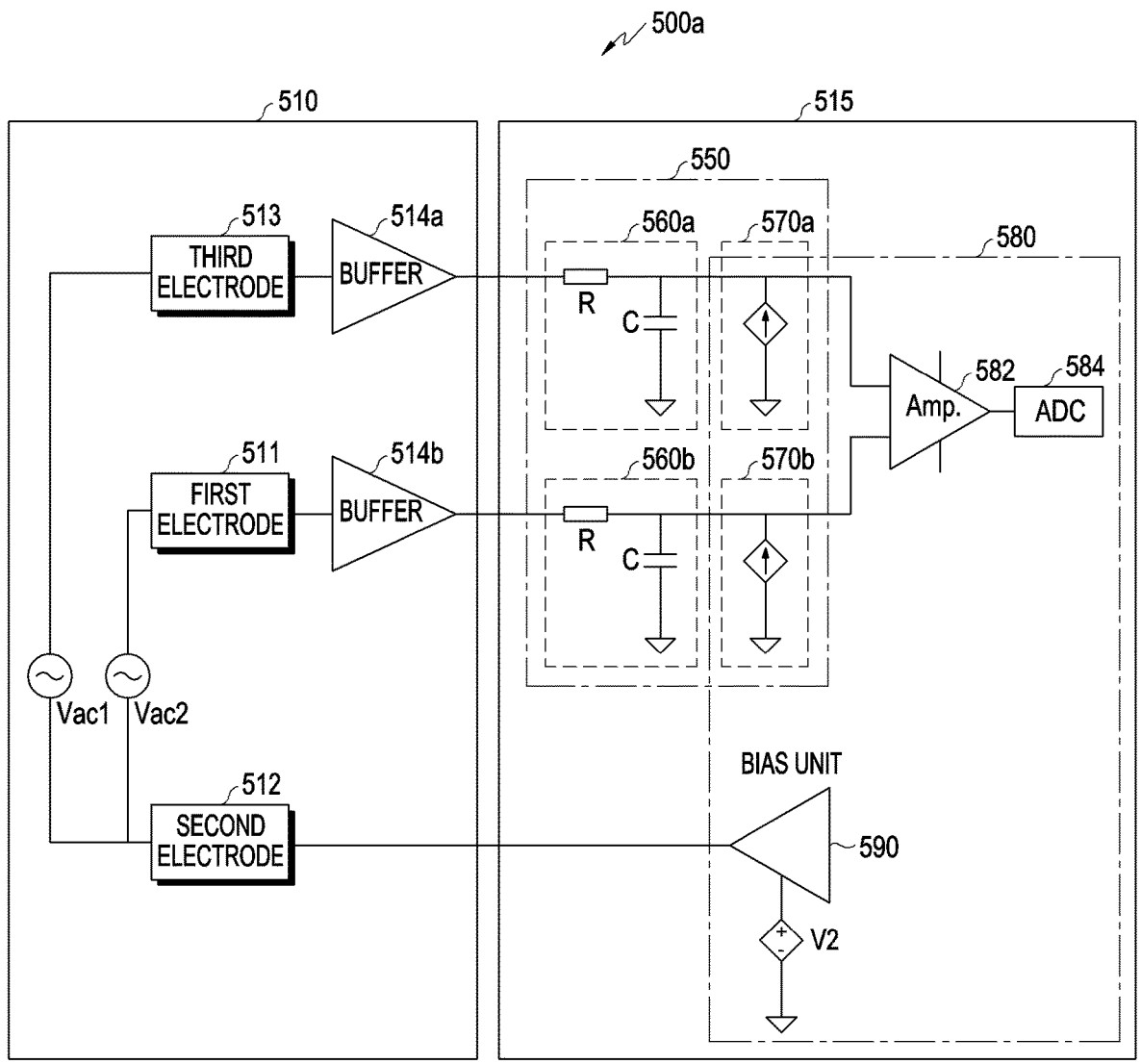
FIG. 5A is a circuit diagram illustrating processing of a biometric signal in a wearable electronic device according to an embodiment of the disclosure.

FIG. 5A is a circuit diagram 500a illustrating processing of a biometric signal in a wearable electronic device according to an embodiment of the disclosure.

FIG. 5A is a circuit diagram of a device for biometric signal processing as shown in FIG. 3. For ease of description, an example is described below in which the biometric signal processing device is a wearable electronic device.

Referring to FIG. 5A, the wearable electronic device may largely include a biometric signal detector 510 and a biometric signal processor 515.

The biometric signal detector 510 may receive biometric signals having different electrical physical quantities from a plurality of electrodes 511, 512, and 513. For example, if a first electrode 511 among the plurality of electrodes 511, 512, and 513 is the electrode for obtaining signals from the wrist of the hand on which the wearable electronic device is worn, the electrode for biopotential biasing for the wrist of the same hand may be a second electrode 512, and an electrode for obtaining signals from the other hand may be a third electrode 513.

The second electrode 512 may apply a DC voltage from a bias unit 590 to the first electrode 511 and the third electrode 513. The bias unit 590 may apply a biopotential offset via the second electrode 512.

As shown in FIG. 5A, after identifying the biocontact at all the electrodes, the potential at the first electrode INP 511 and the potential at the third electrode INN 513 may be transferred to the low pass filters 560a and 560b via their respective corresponding buffers 514a and 514b.

The buffers 514a and 514b are ones for high input impedance and play a role to prevent the cutoff frequencies of the low pass filters 560a and 560b from being influenced by the impedance at each electrode.

The offset correction circuit 550 (e.g., the offset correction circuit 315 of FIG. 3) may include low pass filters 560a and 560b and current sources 570a and 570b. Since R in the low pass filters 560a and 560b is a fixed value, the width of offset adjustment may be varied depending on the magnitude of the current sources 570a and 570b, e.g., the magnitude of current.

The low pass filters 560a and 560b may have a bandwidth for obtaining biometric signals, e.g., ECG signals. According to an embodiment of the disclosure, each low pass filter 560a and 560b may be implemented outside if no anti-aliasing low pass filter is present in the analog front end (AFE) 580 processing biometric signals.

The current sources 570a and 570b may output an adjustable current magnitude. The current source 570a or 570b may output DC currents, be connected with a signal chain via a switch, and play a role to operate as a source or sink. According to an embodiment of the disclosure, the current source 570a or 570b may be connected with the output terminal of the low pass filter 560a or 560b and the input terminal of the differential amplifier 582 via a switch or, alternatively, connection and/or disconnection may be made via adjustment of the magnitude of current of the current source even without a switch.

The analog front end (AFE) 580 may differentially amplify the potential at the first electrode INP 511 and the signal at the third electrode INN 513 and output the resultant signal. The analog front end (AFE) 580 may include a differential amplifier INA 582 and an ADC 584. The potential at the first electrode INP 511 and signal measurement at the third electrode INN 513 may be implemented via a commercial integrated circuit (IC) or may be performed by a processor (e.g., the processor 320 of FIG. 3). According to an embodiment of the disclosure, the analog front end (AFE) 580 may include a switch and a current source manufactured for detecting a lead-off at each input terminal of the differential amplifier INA 582.

According to an embodiment of the disclosure, the offset which is the difference between the two electrodes may be measured using the differential amplifier 582. After the difference between the two electrodes is compared with a predetermined threshold, if it falls within a threshold range with respect to the predetermined threshold, offset correction is not performed but, if it falls out of the threshold range, it may be identified whether the direction of the offset is a + or − direction. Upon determining that the offset, which is the difference between the two electrodes, falls out of the threshold range in the + direction, the analog front end (AFE) 580 may adjust the magnitude of the current from the current source in the direction of decreasing the offset at the first electrode INP 511 or increasing the offset at the third electrode INN 513, thereby shifting the difference between the two electrodes, $V_P$–$V_N$, in the – direction.

In contrast, upon determining that the offset, which is the difference between the two electrodes, falls out of the threshold range in the – direction, the analog front end (AFE) 580 may adjust the magnitude of the current from the current source in the direction of increasing the offset at the first electrode INP 511 or decreasing the offset at the third electrode INN 513, thereby shifting the difference between the two electrodes, $V_P$–$V_N$, in the + direction. As such, for offset correction, the side of offset adjustment and the direction of offset may be varied depending on what electrode of offset is to be adjusted, which direction of the + and – directions the current is to be applied in, and how much the current magnitude is to be adjusted. This is described below with reference to FIGS. 8A and 8B.

Figure 5B:
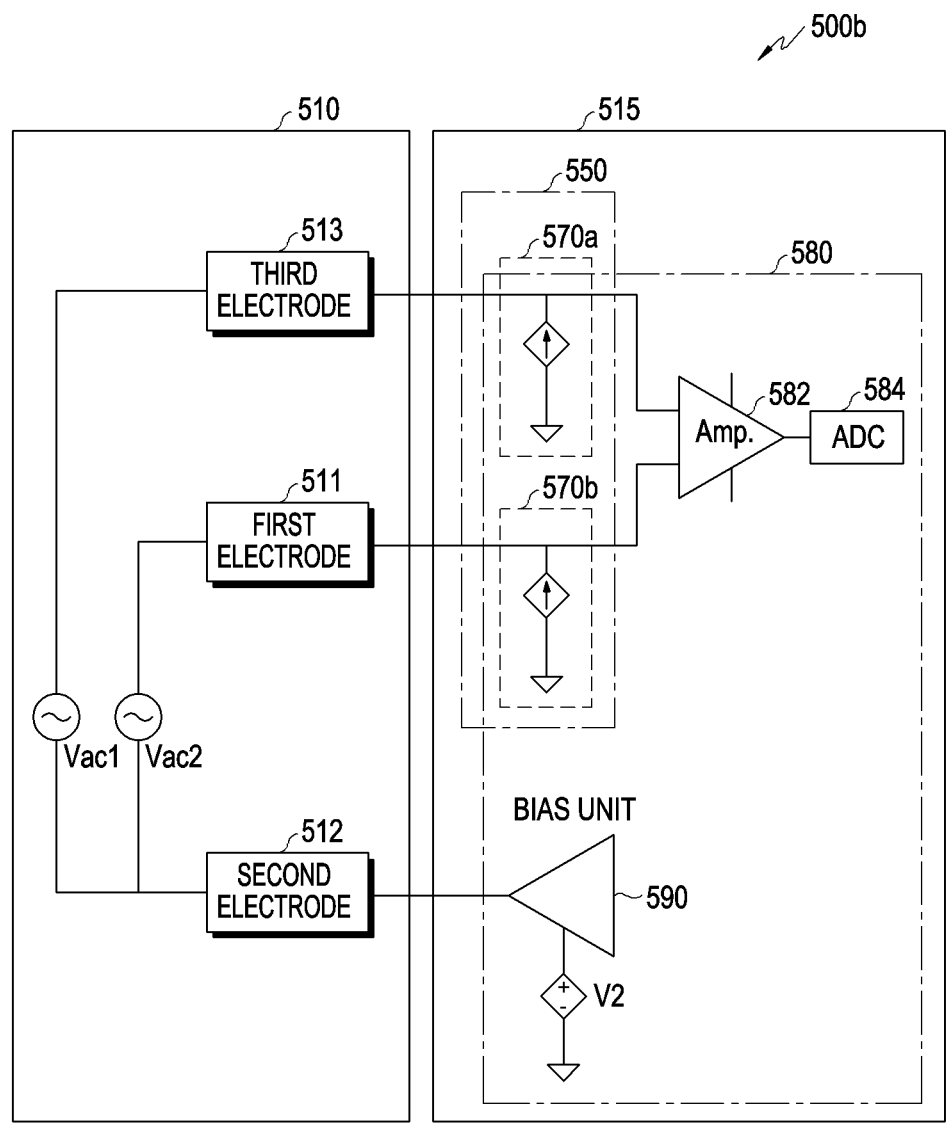
FIG. 5B is a circuit diagram illustrating processing of a biometric signal in a wearable electronic device according to an embodiment of the disclosure.

FIG. 5B is a circuit diagram 500b illustrating processing of a biometric signal in a wearable electronic device according to an embodiment of the disclosure.

As compared with FIG. 5A, in FIG. 5B, the buffers (e.g., the buffers 514a and 514b of FIG. 5A) connected to the respective output terminals of the first electrode 511 and the third electrode 513 and the low pass filters (e.g., the low pass filters 560a and 560b of FIG. 5A) may be omitted.

Referring to FIG. 5B, when an offset correction circuit is implemented with no buffers and low pass filters, the offset correction circuit may include a first current source 570b between the output terminal of the first electrode 511 among the plurality of electrodes and the input terminal of the differential amplifier 582 and a second current source 570a between the output terminal of the third electrode 513 and the input terminal of the differential amplifier 582.

Figure 6A:
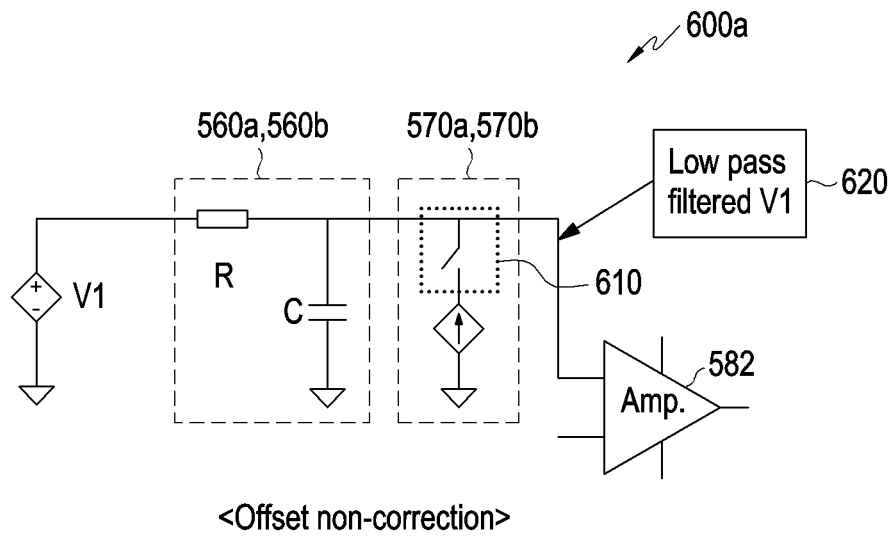
FIG. 6A is a circuit diagram illustrating operations upon offset non-correction according to an embodiment of the disclosure.

FIG. 6A is a circuit diagram 600a illustrating operations upon offset non-correction according to an embodiment of the disclosure.

Referring to FIG. 6A, an electrode potential V1 output from a buffer (e.g., the buffer 514a or 514b of FIG. 5A) connected to the output terminal of an electrode may pass through a low pass filter (e.g., the low pass filter 560a or 560b of FIG. 5A) and be applied to the input terminal of a differential amplifier 582 (e.g., INA). Thus, V1 620 which has passed through the low pass filter may be applied to the input terminal of the differential amplifier 582 (e.g., INA). In this case, since no current is generated at the current source ILEADOFF (e.g., the current source 570a or 570b of FIG. 5A or 5B), i.e., OFF state, the current source 570a or 570b may be in such a state where the low pass filter 560a or 560b is disconnected from the differential amplifier 582. For example, the current source ILEADOFF 570a or 570b may turn on/off the connection with the differential amplifier 582 and the low pass filter 560a or 560b as does the switch 610.

Figure 6B:
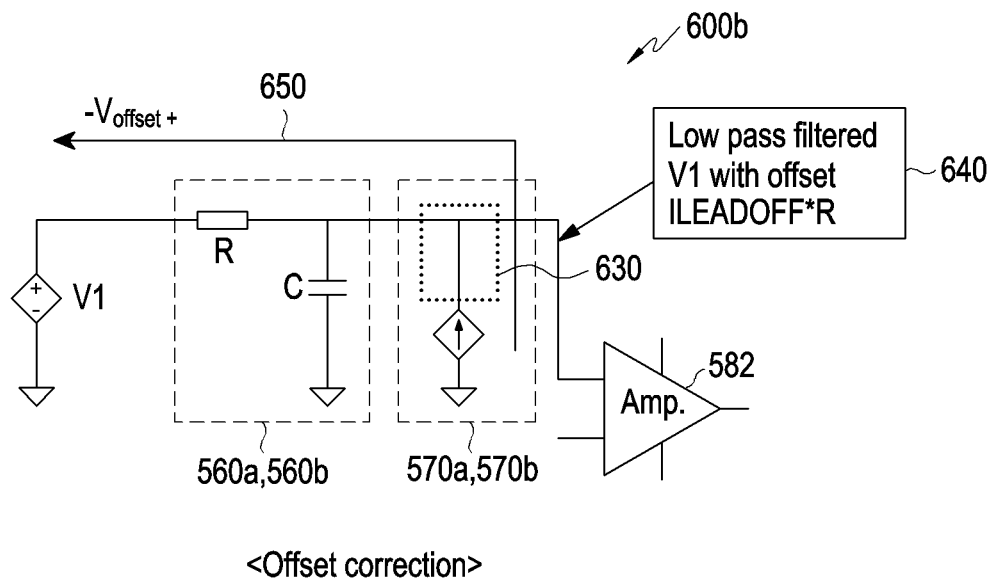
FIG. 6B is a circuit diagram illustrating operations upon offset correction according to an embodiment of the disclosure.

FIG. 6B is a circuit diagram 600b illustrating operations upon offset correction according to an embodiment of the disclosure.

Referring to FIG. 6B, when offset correction is operated, the current source ILEADOFF 570a or 570b outputs a DC current, so that the current from the current source ILEADOFF 570a or 570b may be applied in the electrode direction 650 like a switch is shorted (630). At this time, the current from the current source ILEADOFF 570a or 570b is as small as neglectable due to the input of the differential amplifier 582 which has a very high input impedance and, by analysis of the DC component, the capacitor C of the low pass filter 560a or 560b may be regarded as open. Thus, the current from the current source ILEADOFF 570a or 570b may come out to the ground through the resistor R of the low pass filter 560a or 560b and the output terminal of the buffer (e.g., the buffer 514a or 514b of FIG. 5A). Thus, a potential whose magnitude is (ILEADOFF*R) may be formed at the resistor R by the current from the current source ILEADOFF 570a or 570b, and the voltage applied to the input terminal of the differential amplifier 582 may become V1+(ILEADOFF*R) (640).

As such, the voltage applied to the input terminal of the differential amplifier 582 may be adjusted by applying the offset to the signal V1 output from the electrode according to the contact of biometric signal and, by such adjustment, i.e., offset correction, a signal may be obtained which falls within the reference voltage range (or threshold voltage range).

According to an embodiment of the disclosure, the current from the current source may be variable, and current magnitude may be stepwise adjusted. According to an embodiment of the disclosure, not only may DC offset adjustment at a single channel (e.g., one electrode) be possible, but simultaneous DC offset adjustment at multiple channels (e.g., at least two electrodes) may be possible as well. According to an embodiment of the disclosure, offset adjustment may be performed by selecting any one from among values of several operations, and the direction of offset adjustment may be controlled by adjusting the polarity, e.g., in the positive or negative direction. The above-described operation selection for offset correction may be performed under the control of the analog front end (AFE) processing biometric signals or, alternatively, it may be performed under the control of the processor of the wearable electronic device.

Figure 7:
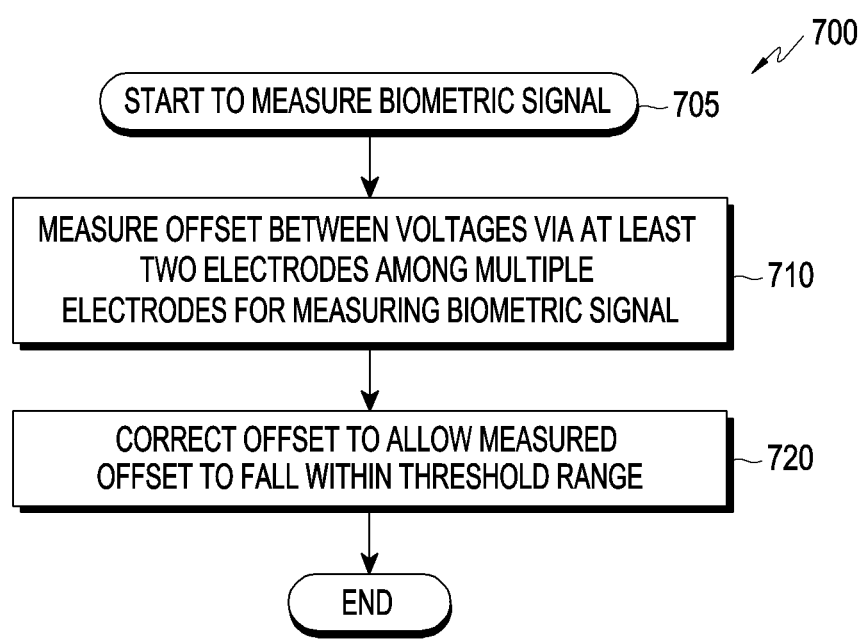
FIG. 7 is a flowchart illustrating operations for biometric signal processing in a wearable electronic device according to an embodiment of the disclosure.

FIG. 7 is a flowchart 700 illustrating operations for biometric signal processing in a wearable electronic device according to an embodiment of the disclosure.

Referring to FIG. 7, the operation method may include operations 705 to 720. Each operation of the operation method of FIG. 7 may be performed by at least one of a wearable electronic device (e.g., the electronic device 101 of FIG. 1A or the biometric signal processing device 301 of FIG. 3) or at least one processor (e.g., the processor 120 of FIG. 1A and the processor 320 of FIG. 3) of the wearable electronic device. According to an embodiment of the disclosure, at least one of operations 705 to 720 may be omitted, some operations thereof may be performed in reverse order, or other operations may be added thereto.

In operation 705, the wearable electronic device may start to measure a biometric signal.

According to an embodiment of the disclosure, when a wearing of the wearable electronic device on the user's body is detected, a signal of the detection may be determined to be an 'input or request for measurement.' For example, when signals input via a plurality of electrodes (e.g., the first electrode to third electrode 511, 512, and 513 of FIGS. 5A and 5B) included in the wearable electronic device are first received when the wearable electronic device is attached to the user's body, the wearable electronic device may determine that the first received signals are an 'input or request for measurement.'

According to an embodiment of the disclosure, when its wearing is detected, the wearable electronic device may automatically switch to a mode for biometric signal measurement and start measurement. Alternatively, the start and end of measurement of the biometric signal in the wearable electronic device may be controlled manually according to the user's selection in the wearable electronic device or an electronic device (e.g., a smartphone) interworking with the wearable electronic device or, alternatively, measurement may be allowed to automatically start using the on/off function.

As described above, when biometric signal measurement starts, an offset between voltages may be measured via at least two electrodes among a plurality of electrodes for measuring the biometric signal in the wearable electronic device in operation 710. For example, the wearable electronic device may measure the ECG signal using signals output as a signal for the user's first portion (e.g., wrist) is output via the first electrode and second electrode, which are adjacent to each other, and a signal for the user's second portion (e.g., finger) is output via the third electrode. According to an embodiment of the disclosure, a need exists for obtaining a stable ECG signal regardless of the difference between the two electrodes due to various measurement environments upon measuring ECG, and the wearable electronic device may perform offset correction to be able to obtain such an ECG signal. In operation 720, the wearable electronic device may correct the offset to allow the measured offset to fall within the threshold range.

According to an embodiment of the disclosure, a method for processing a biometric signal in a wearable electronic device comprises measuring an offset between voltages via at least two electrodes among a plurality of electrodes for measuring the biometric signal in the wearable electronic device and correcting the offset to allow the measured offset to fall within a threshold range.

According to an embodiment of the disclosure, the method may further comprise measuring, using a differential amplifier, the offset between a first voltage via a first electrode among the at least two electrodes and a second voltage via a third electrode, with respect to a reference voltage, as the reference voltage is applied via a second electrode among the plurality of electrodes and, when the measured offset falls out of the threshold range, correcting the offset.

According to an embodiment of the disclosure, correcting the offset may include, when the measured offset falls out of the threshold range, correcting the offset by adjusting a current magnitude of any one of a first current source, between an output terminal of the first electrode and an input terminal of the differential amplifier, and a second current source, between an output terminal of the third electrode and an input terminal of the differential amplifier, for a voltage for the first electrode and a voltage for the third electrode.

According to an embodiment of the disclosure, the method may further comprise, when the measured offset is larger than an upper limit threshold of the threshold range, correcting the offset by applying a second current of the second current source in a direction towards the third electrode to increase the voltage for the third electrode and decrease the voltage for the first electrode.

According to an embodiment of the disclosure, the method may further comprise, when the measured offset is smaller than a lower limit threshold of the threshold range, correcting the offset by applying a first current of the first current source in a direction towards the first electrode to decrease the voltage for the third electrode and increase the voltage for the first electrode.

Figure 8A:
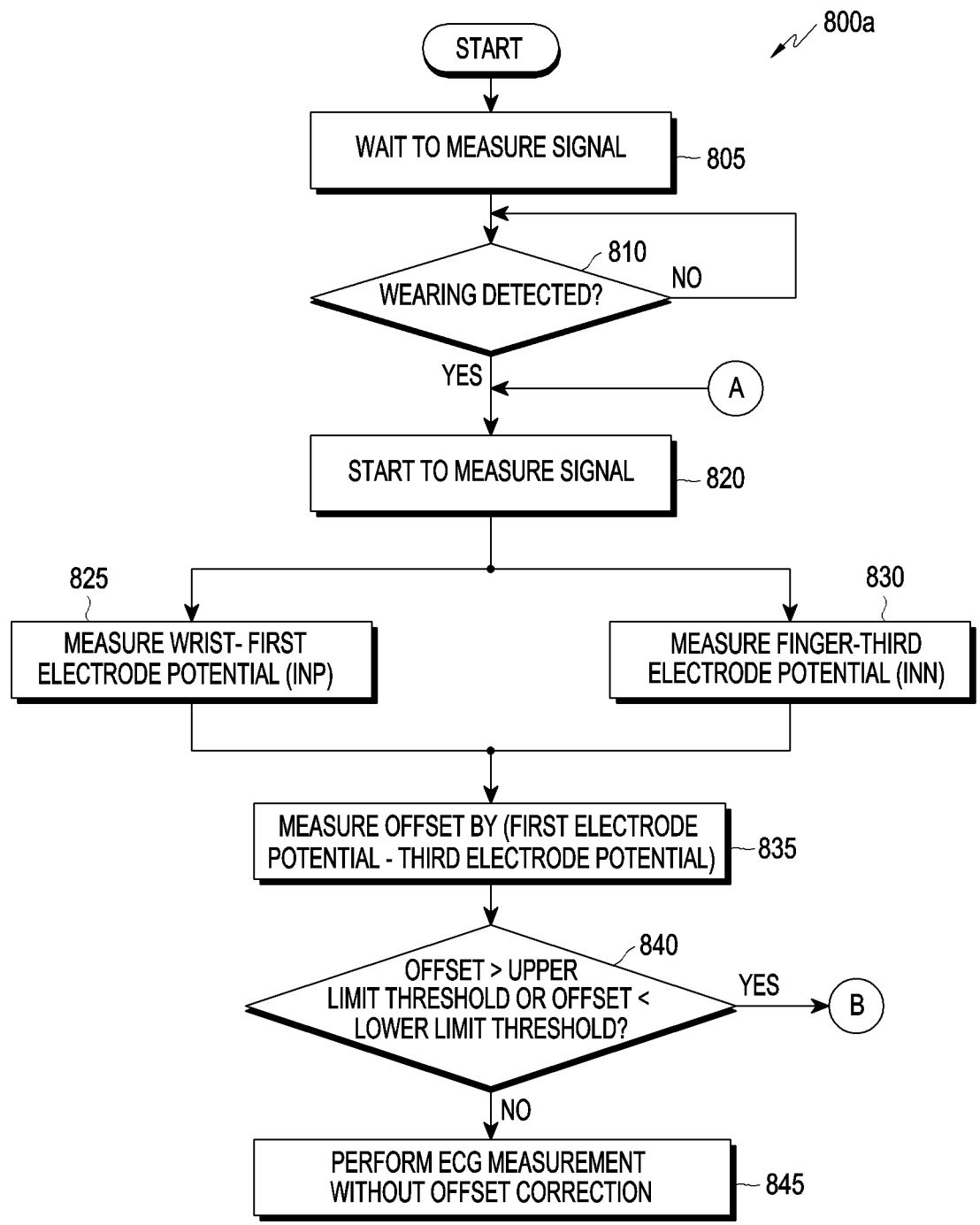
FIG. 8A is a flowchart illustrating biometric signal processing operations in a wearable electronic device according to an embodiment of the disclosure.

FIG. 8A is a flowchart 800a illustrating biometric signal processing operations in a wearable electronic device according to an embodiment of the disclosure.

Figure 8B:
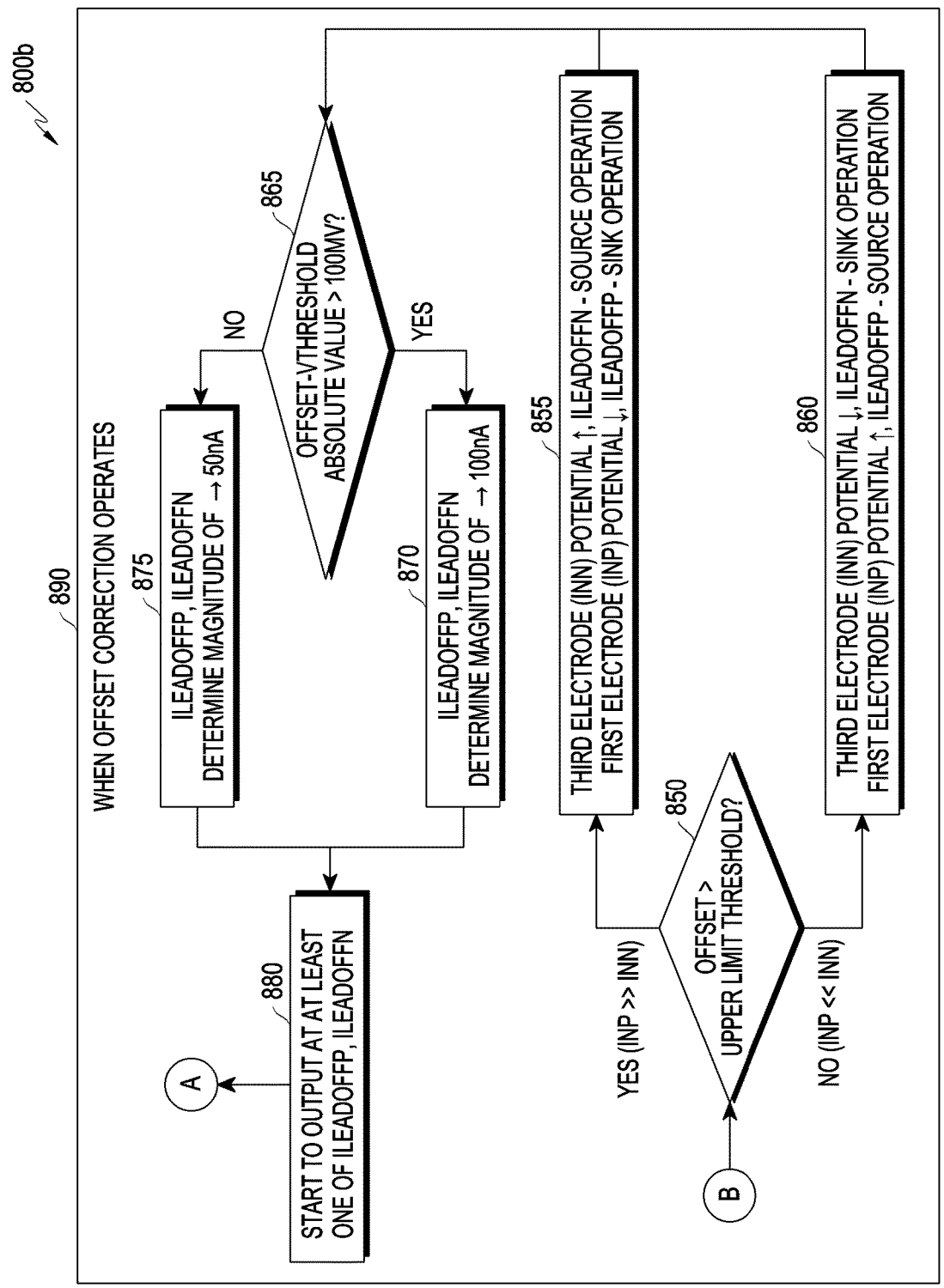
FIG. 8B is a flowchart illustrating offset correction operations in a wearable electronic device according to an embodiment of the disclosure.

FIG. 8B is a flowchart 800b illustrating offset correction operations in a wearable electronic device according to an embodiment of the disclosure.

Referring to FIG. 8A, the operation method may include operations 805 to 845 and, referring to FIG. 8B, the operation method may include operations 850 to 880. Here, symbol B may be used to indicate that operation 840 of FIG. 8A is connected with operation 850 of FIG. 8B, and symbol A may be used to indicate that operation 880 of FIG. 8B is connected with operation 820 of FIG. 8A.

Each operation of the operation method of FIGS. 8A and 8B may be performed by at least one of a wearable electronic device (e.g., the electronic device 101 of FIG. 1A or the biometric signal processing device 301 of FIG. 3) or at least one processor (e.g., the processor 120 of FIG. 1A and the processor 320 of FIG. 3) of the wearable electronic device. According to an embodiment of the disclosure, at least one of operations 805 to 880 may be omitted, some operations thereof may be performed in reverse order, or other operations may be added thereto.

Referring to FIG. 8A, in the state of waiting to measure a biometric signal in operation 805, the wearable electronic device may detect whether it is worn in operation 810. According to an embodiment of the disclosure, whether the wearable electronic device is worn may be detected as signals are first received via at least two electrodes for biometric signal measurement, and in the state where whether it is worn has been detected, e.g., in the state of contacting a first portion (e.g., wrist) of the living body, ECG signal measurement may be started based on signals output as a second portion (e.g., finger) of the living body contacts the third electrode (e.g., the third electrode 513 of FIGS. 5A and 5B).

For example, when the user wears the wearable electronic device and then runs an application (e.g., ECG application) related to biometric signal measurement, the wearable electronic device may continuously or periodically identify whether the living body contacts the electrodes. As such, when signals are output as all of the first electrode to the third electrode are contacted, biometric signal measurement may start. Other methods for detecting a wearing and starting measurement than those described above have been described in connection with FIG. 7, and no further detailed description thereof is given below.

As a finger contacts the third electrode with a wrist contacting the first electrode and the second electrode, the wearable electronic device may start to measure a biometric signal in operation 820. According to an embodiment of the disclosure, biometric signal measurement may be started automatically or by the user's selection. Thus, in operation 825, the wearable electronic device may measure the potential at the first electrode for the first portion (e.g., wrist) of the living body and, in operation 830, the potential at the third electrode for the second portion (e.g., finger) of the living body may be measured. When a closed loop is formed between the user's body and the wearable electronic device, the second electrode may play a role to adjust the bias of the wearable electronic device and the user's body. To that end, the second electrode (e.g., the second electrode 512 of FIGS. 5A and 5B) may be used as a reference electrode. As a reference voltage is applied to the second electrode, the potential difference (e.g., voltage Vac2 of FIGS. 5A and 5B) at the first electrode (e.g., the first electrode 511 of FIGS. 5A and 5B) from the reference electrode may be measured, and the potential difference (e.g., voltage Vac1 of FIGS. 5A and 5B) at the third electrode from the same reference electrode may be measured.

According to an embodiment of the disclosure, the wearable electronic device may measure the potential at each electrode using a first buffer (e.g., the buffer 514b of FIG.

5A) for the first electrode and a third buffer (e.g., the buffer 514a of FIG. 5A) for the third electrode. The second electrode (e.g., the second electrode 512 of FIGS. 5A and 5B) may be an electrode for biopotential biasing for the first portion (e.g., wrist) of the living body. The potential at the first electrode may be measured with respect to the second electrode, and the potential at the third electrode may be measured with respect to the same second electrode, so that the potential difference between the first electrode and the third electrode may be measured.

In operation 835, the wearable electronic device may measure offset due to the difference between the potential at the first electrode and the potential at the third electrode. According to an embodiment of the disclosure, the wearable electronic device may measure the potential difference between the first electrode and the third electrode by applying the same voltage to each of the first electrode and the third electrode via the second electrode. According to an embodiment of the disclosure, the wearable electronic device may measure a differential signal, i.e., the potential difference between the two electrodes, using a differential amplifier (internal instrumentation amplifier) (e.g., INA). According to an embodiment of the disclosure, the difference between the first electrode and the third electrode may be referred to as a potential difference, voltage difference, direct current (DC) difference, offset, or DC offset.

In operation 840, the wearable electronic device may determine (or identify) whether the offset is larger than the upper limit threshold or whether the offset is smaller than the lower limit threshold. According to an embodiment of the disclosure, the upper limit threshold and the lower limit threshold may be the upper limit and lower limit, respectively, of a reference voltage range. Here, the reference voltage range may be a predetermined threshold voltage range for determining whether offset correction is performed or may also be referred to as an input dynamic range. The reference voltage range may be predetermined when the wearable electronic device is shipped out or, alternatively, may be newly determined considering the measurement environment before the biometric signal measurement or whenever an application (e.g., an ECG application) for biometric signal measurement is executed.

According to an embodiment of the disclosure, upon determining that the offset is larger than the upper limit threshold or is not smaller than the lower limit threshold, e.g., upon determining that the offset falls within the reference voltage range, the wearable electronic device may measure the biometric signal without offset correction in operation 845. For example, when the potentials at the first electrode and the third electrode are measured, and the potential difference falls within the reference voltage range, the biometric signal may be obtained as the two signals pass through the differential amplifier (e.g., the amplifier 582 of FIGS. 5A and 5B) and then the ADC (e.g., the ADC 584 of FIGS. 5A and 5B). According to an embodiment of the disclosure, the biometric signal measurement may be measurement of an ECG signal. Thus, the wearable electronic device may continuously or periodically perform biometric signal measurement, so that the above-described operations may be continuously or periodically repeated unless the execution of the application (e.g., an ECG application) for biometric signal measurement is terminated. Thus, it is possible to continuously determine whether the offset between the two electrodes measured while measuring the biometric signal without offset correction falls out of the upper limit threshold and lower limit threshold.

According to an embodiment of the disclosure, upon determining that the offset is larger than the upper limit threshold or smaller than the lower limit threshold, e.g., upon determining that the offset falls out of the reference voltage range, the wearable electronic device may perform the offset correction operation (890) of FIG. 8B.

Upon determining that the offset is larger than the upper limit threshold or smaller than the lower limit threshold, the wearable electronic device may determine whether the offset is larger than the upper limit threshold in operation 850 of FIG. 8B. Upon determining that the offset is larger than the upper limit threshold, the wearable electronic device may perform correction to allow the offset to fall within the reference voltage range.

According to an embodiment of the disclosure, in order for the offset to fall within the reference voltage range, the wearable electronic device may adjust, in real-time, at least one of the potential (or voltage) (e.g., $V_P$) at the first electrode or the potential (or voltage) (e.g., $V_N$) at the third electrode, thereby performing offset correction. As such, as offset correction is performed in real-time during the biometric signal measurement, a stable biometric signal may be obtained. Thus, the wearable electronic device may allow signals to be stably output via two electrodes within a predetermined voltage range although the magnitude of the signals input via the two electrodes is not constant due to the issue with various biometric signal measurement environments, as well as electrode materials, thereby allowing for more reliable biometric signal analysis.

According to an embodiment of the disclosure, offset correction may be performed largely in three manners.

First, the wearable electronic device may perform offset correction by adjusting the voltage at any one of the first electrode to the third electrode.

Second, the wearable electronic device may perform offset correction by applying current in any one direction towards the first electrode and the third electrode.

Finally, the wearable electronic device may perform offset correction by determining what magnitude the offset is to be adjusted in.

According to an embodiment of the disclosure, in order for the offset to fall within the reference voltage range, the wearable electronic device may adjust at least one of the potential (or voltage) (e.g., $V_P$) at the first electrode or the potential (or voltage) (e.g., $V_N$) at the third electrode or apply current to any one of the two electrodes, thereby performing offset correction. In this case, the magnitude of the offset to be adjusted may be determined to differ by the magnitude of the current to be applied.

The potential (or voltage) (e.g., $V_P$) at the first electrode and the potential (or voltage) (e.g., $V_N$) at the third electrode are described below with reference to FIG. 9.

Figure 9:
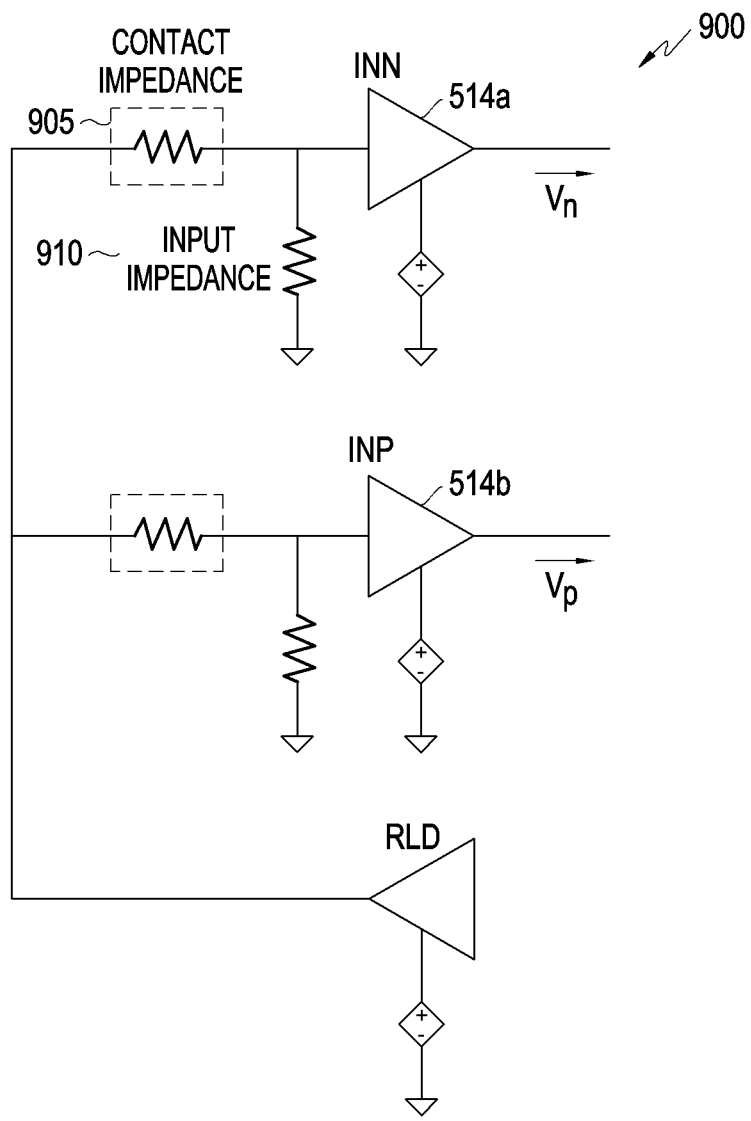
FIG. 9 is a circuit diagram illustrating a relationship between contact impedance and input impedance according to an embodiment of the disclosure.

FIG. 9 is a circuit diagram 900 illustrating a relationship between contact impedance and input impedance according to an embodiment of the disclosure.

Referring to FIG. 9, when the third electrode for a finger is an N electrode, and the first electrode for a wrist is a P electrode in the wearable electronic device, the P electrode for the wrist, which is relatively large and remains in contact with the skin for a long time, may have a low contact resistance. In contrast, the finger N electrode makes a new contact at every moment and may thus have a relatively high resistance as compared with the wrist P electrode. Thus, the DC voltages caused at the P electrode and the N electrode may be determined by a ratio of the contact impedance 905 to the input impedance 910 as shown in FIG. 9. Thus, the potential (or voltage) (e.g., $V_N$) at the third electrode may be lower than the potential (or voltage) (e.g., $V_P$) at the first electrode, due to the difference in contact impedance between the wrist P electrode and the finger N electrode.

Upon determining that the offset is larger than the upper limit threshold in operation 850 of FIG. 8B, the wearable electronic device may control to decrease the potential at the first electrode while increasing the potential at the third electrode in operation 855, for offset correction. Upon determining that the offset is larger than the upper limit threshold, the wearable electronic device may recognize that the direction of the offset is a + direction or a − direction and operate the first electrode INP as a sink and may determine whether to operate the third electrode INN as a source or in the opposite manner.

This is described below with reference to FIG. 10A.

Figure 10A:
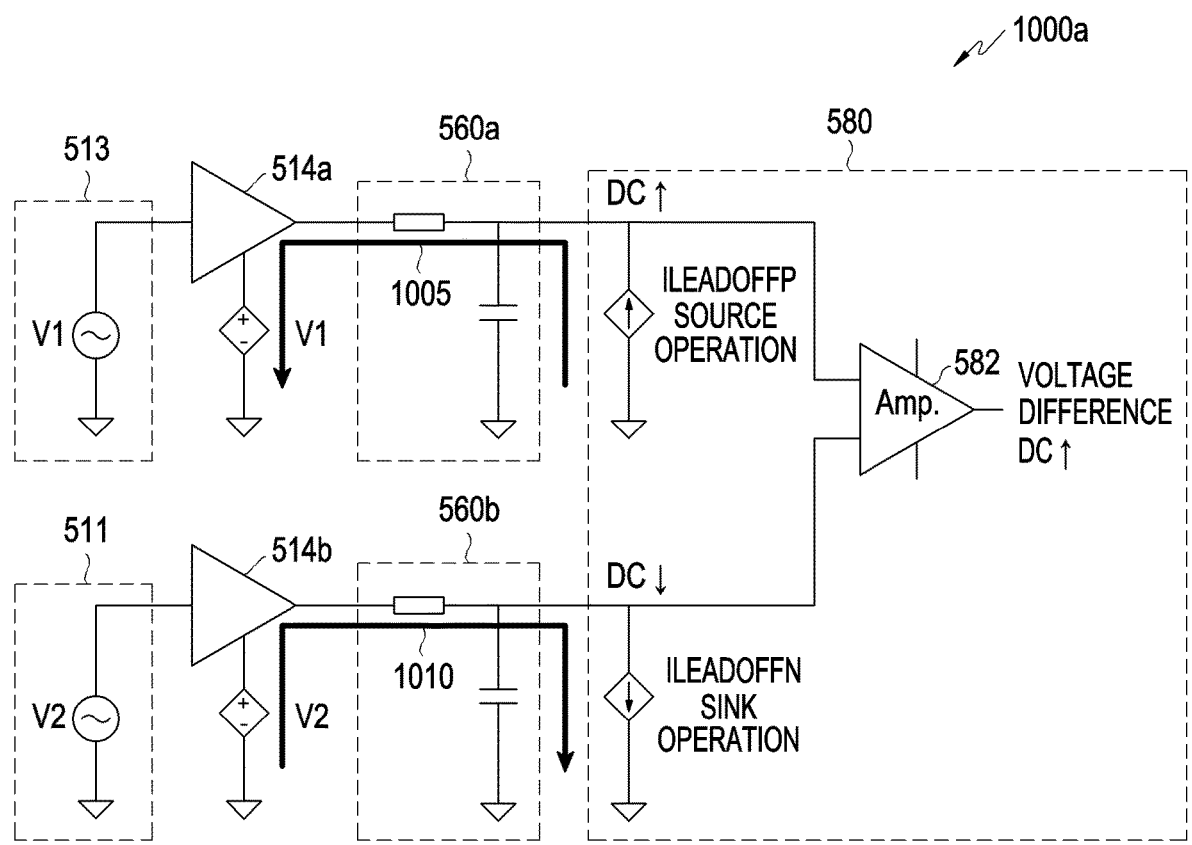
FIG. 10A is a circuit diagram illustrating a first electrode being set to operate as a sink and a third electrode is set to operate as a source, according to an embodiment of the disclosure.

FIG. 10A is a circuit diagram 1000a illustrating setting of a first electrode (e.g., the first electrode 511 of FIGS. 5A and 5B) to operate as a sink and a third electrode (e.g., the third electrode 513 of FIGS. 5A and 5B) to operate as a source, according to an embodiment of the disclosure.

Referring to FIG. 10A, the wearable electronic device may increase the potential at the third electrode 513 (or the DC voltage from the third electrode 513) by allowing the current source (e.g., the current source 570a of FIGS. 5A and 5B) connected with the third electrode 513 to operate as a source and applying the current (e.g., ILEADOFFN) of the current source 570a in a direction 1005 towards the third electrode 513. Simultaneously, by allowing the current source (e.g., the current source 570b of FIGS. 5A and 5B) connected with the first electrode 511 to operate as a sink, the wearable electronic device may reduce the potential for the first electrode 511 (or the DC voltage from the first electrode 511) by the current (e.g., ILEADOFFP) of the current source 570b as the voltage at the first electrode 511 passes (1010) through the resistor R of the low pass filter 560b. The potential for the first electrode 511 (or the DC voltage from the first electrode 511) may be reduced to the product of the current (e.g., ILEADOFFP) of (current source 570b) and resistance R of the low pass filter 560b.

In contrast, when the offset is not larger than the upper limit threshold, e.g., when the offset is smaller than the lower limit threshold in operation 850, it may control to increase the potential at the first electrode while decreasing the potential at the third electrode in operation 860. This is described below with reference to FIG. 10B.

Figure 10B:
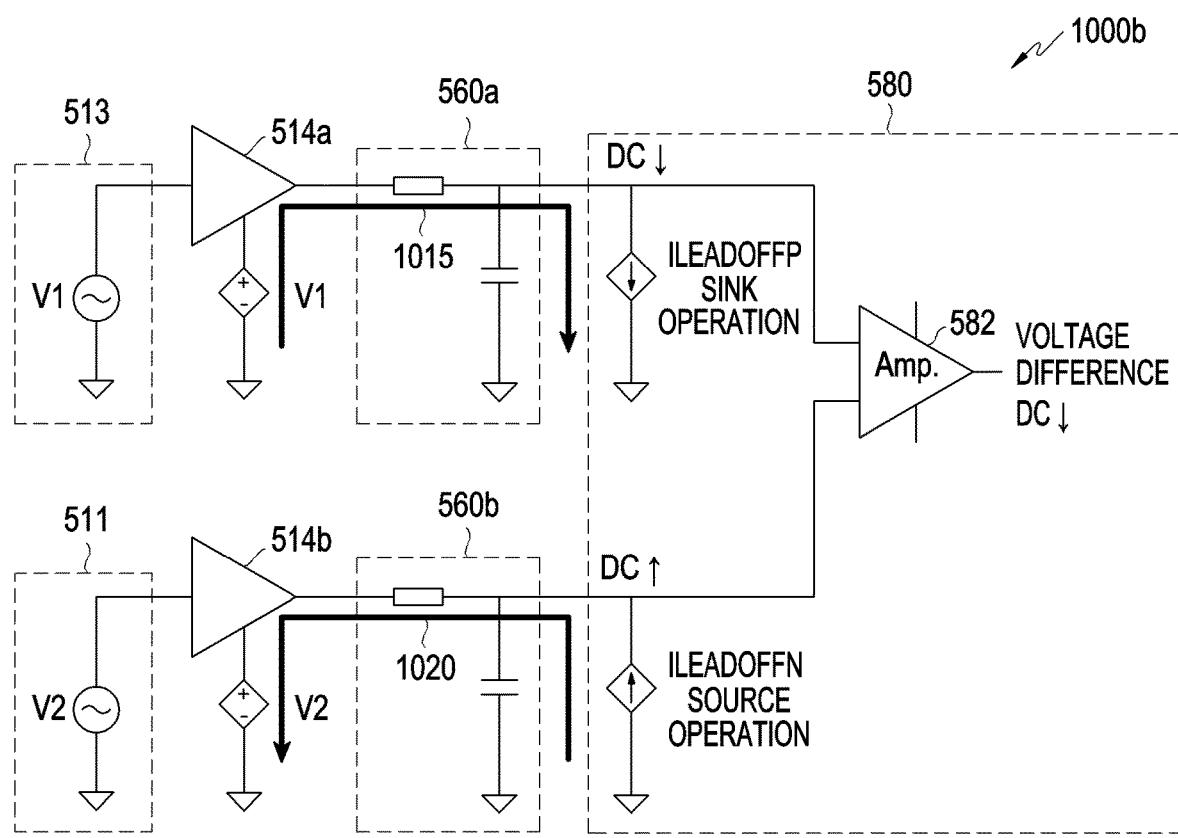
FIG. 10B is a circuit diagram illustrating a first electrode being set to operate as a source and a third electrode is set to operate as a sink, according to an embodiment of the disclosure.

FIG. 10B is a circuit diagram 1000b illustrating setting of a first electrode (e.g., the first electrode 511 of FIGS. 5A and 5B) to operate as a source and a third electrode (e.g., the third electrode 513 of FIGS. 5A and 5B) to operate as a sink, according to an embodiment of the disclosure.

Referring to FIG. 10B, by allowing the current source (e.g., the current source 570a of FIGS. 5A and 5B) connected with the third electrode 513 to operate as a sink, the wearable electronic device may reduce the potential for the third electrode 513 (or the DC voltage from the third electrode 513) by the current (e.g., ILEADOFFN) of the current source 570a as the voltage at the third electrode 513 passes (1015) through the resistor R of the low pass filter (e.g., the low pass filter 560a of FIG. 5A). Simultaneously, upon allowing the current source 570b connected with the first electrode 511 to operate as a source, the wearable electronic device may increase the potential at the first electrode 511 (or the DC voltage from the first electrode 511) by applying the current (e.g., ILEADOFFP) of the current source 570b in the direction (1020) towards the first electrode 511. The potential for the third electrode 513 (or the DC voltage from the third electrode 513) may be reduced to the product of the current (e.g., ILEADOFFN) of (current source 570a) and resistance R of the low pass filter 560a.

As described above, in operations 855 and 860, as the operation of adjusting the offset by controlling the direction of current, the offset at the corresponding electrode may be increased to (current of current source*resistance (R) of low pass filter) in the case where the current of the current source is operated as a source as in operation 855 and, when operated as a sink, the offset may be reduced by the same level.

By adjusting, in real-time, the offset in the above-described manner, it may be determined whether the adjusted offset falls within the reference voltage range and, unless it falls within the reference voltage range, it may be determined whether to further adjust the offset.

The wearable electronic device may determine how much the current of the current source is to be adjusted to allow the adjusted offset to fall within the reference voltage range. In this case, since the resistance R of the low pass filter is a pre-fixed value, when the magnitude of the current of the current source is adjusted, the magnitude of offset adjustment may also be determined.

To that end, the wearable electronic device may determine whether the difference between the offset and a predetermined threshold (e.g., Vthreshold) is larger than an offset adjustment unit (e.g., 100 mV) in operation 865. When the difference between the offset and the predetermined threshold (e.g., Vthreshold) is larger than the offset adjustment unit, the wearable electronic device may determine that the respective magnitudes of the current (e.g., ILEADOFFN) of the current source (e.g., the current source 570a of FIGS. 5A and 5B) and the current (e.g., ILEADOFFP) of the current source (e.g., the current source 570b of FIGS. 5A and 5B) are a first magnitude (e.g., 100 nA) so as to increase the magnitude of offset adjustment, in operation 870. In contrast, when the difference between the offset and the predetermined threshold (e.g., Vthreshold) is not larger than the offset adjustment unit, the wearable electronic device may determine that the respective magnitudes of the current (e.g., ILEADOFFN) of the current source (e.g., the current source 570a of FIGS. 5A and 5B) and the current (e.g., ILEADOFFP) of the current source (e.g., the current source 570b of FIGS. 5A and 5B) are a second magnitude (e.g., 50 nA), in operation 875. Here, the second magnitude may be smaller than the first magnitude.

In the described example, since the resistance R is 1 MΩ and, as the currents (e.g., ILEADOFF(P,N)) of the current source, 50 nA and 100 nA are used, the offset adjustment is performed in two operations, e.g., 100 mV and 200 mV. However, the offset adjustment operations are not limited thereto. For example, offset adjustment may be performed in proportion, corresponding to the magnitude of current of the current source, and this is described below with reference to FIG. 13.

Thus, in operation 880, at least one of the current (e.g., ILEADOFFN) of the current source (e.g., the current source 570a of FIGS. 5A and 5B) and the current (e.g., ILEADOFFP) of the current source (e.g., the current source 570b of FIGS. 5A and 5B) may start to be output. As in operation 880, as at least one of the current (e.g., ILEADOFFN) of the current source (e.g., the current source 570a of FIGS. 5A and 5B) and the current (e.g., ILEADOFFP) of the current source (e.g., the current source 570b of FIGS. 5A and 5B) is applied to the first electrode or third electrode, the potential at each electrode may be varied. Thus, the wearable electronic device may go back to operation 820 to restart biometric signal measurement. Such biometric signal measurement may be periodically performed or, alternatively, continuously while the application is running.

According to an embodiment of the disclosure, the offset voltage may be adjusted stepwise and, when the current may be applied at several magnitudes from the current source (e.g., the current source 570a and current source 570b of FIGS. 5A and 5B), the offset may be adjusted in the offset adjustment magnitude of the product of the resistance R of the low pass filter and the current. In this case, the offset may be adjusted in such a manner that the product of the resistance R of the low pass filter and the current of the current source is added to or subtracted from the voltage for each electrode (e.g., first electrode or third electrode), depending on whether it operates as a source or sink.

Meanwhile, the voltage for each electrode (e.g., first electrode or third electrode) may be adjusted via offset correction. As described above in connection with FIG. 9, before biometric signal measurement starts, the potential (or voltage) (e.g., $V_N$) at the third electrode may be lower than the potential (or voltage) (e.g., $V_P$) at the first electrode due to the difference in contact impedance between the two electrodes, e.g., the wrist P electrode and the finger N electrode.

The difference in contact impedance may be caused by wearing and measuring methods. Further, the difference in contact impedance may also be caused by the electrode material and electrode size. For example, in the case of a wearable electronic device, upon obtaining a biometric signal, an electrode on the side surface may be contacted by a finger only when measurement is performed and, when no measurement is performed, there may be no finger contact. In contrast, since the wearable electronic device is of a watch type, it remains worn on wrist and, in such a wearing state, the contact impedance may be reduced due to the sweat at the interface between the user's skin and the contacting material. Thus, after the wearable electronic device is worn, the contact impedance for the wrist P electrode may gradually reduce, and the contact impedance for the finger N electrode may remain high and, only during the measurement, gradually vary. Thus, the difference in contact impedance may be influenced by various factors, such as the size and material of the electrode, and measurement environment.

Thus, it is possible to obtain a stable biometric signal by shifting the offset, which indicates a difference between the electrodes, as well as the contact impedance varied by various factors, to fall within the reference voltage range by offset correction.

Obtaining a biometric signal via offset correction as described above is described below with reference to FIGS. 11A to 11C.

FIG. 11A is a view 1100a illustrating a signal upon offset non-correction according to an embodiment of the disclosure.

According to an embodiment of the disclosure, the biometric signal may be an ECG signal. FIG. 11A is a graph of a signal obtained upon using the result of $V_P$–$V_N$ which is the difference between the two electrodes as an input to an analog-to-digital converter (ADC).

Referring to FIG. 11A, when the difference between the two electrodes (e.g., the difference between the potential (or voltage) (e.g., $V_N$) at the third electrode and the potential (or voltage) (e.g., $V_P$) at the first electrode falls within a reference voltage range, e.g., the input dynamic range, which has an upper limit threshold and lower limit threshold with respect to a predetermined threshold (e.g., Vthreshold) as a biometric signal is measured in real-time, offset correction may not be needed. However, when no offset correction is performed, such an occasion (1105) where it happens to be in the saturation region as time elapses may occur and, after the saturated time 1105, all the signals may have the same value. Thus, the biometric signal may not be identified, so that the performance of biometric signal measurement may be deteriorated.

Figure 11B:
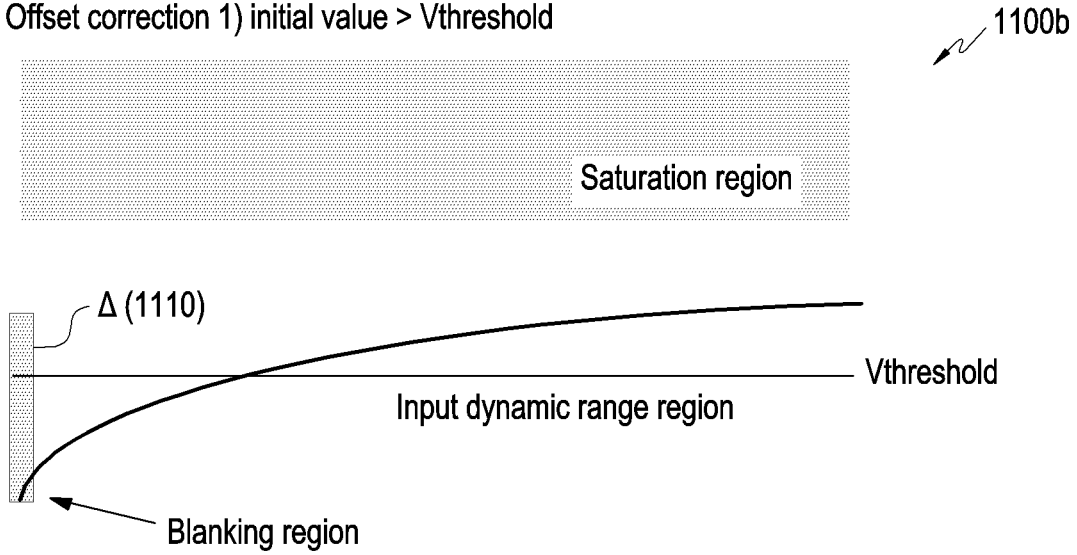
FIG. 11B is a view illustrating a signal upon offset correction via adjustment of an initial value according to an embodiment of the disclosure.
Figure 11C:
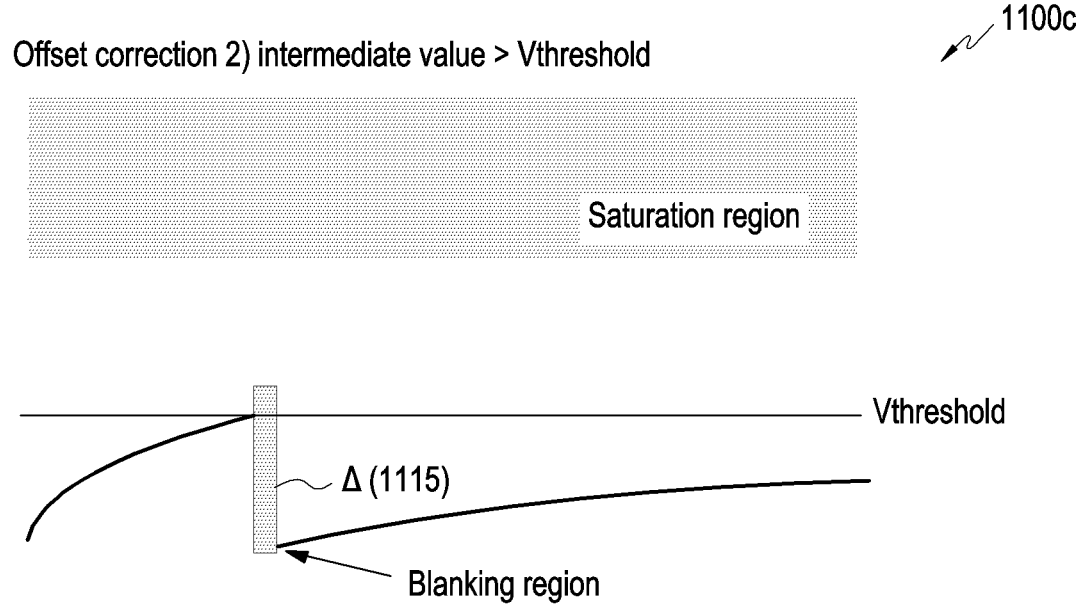
FIG. 11C is a view illustrating a signal upon offset correction via adjustment of an intermediate value according to an embodiment of the disclosure.

FIG. 11B is a view (1100b) illustrating a signal upon offset correction via adjustment of an initial value according to an embodiment. FIG. 11B is identical to FIG. 11A in that the result of $V_P$–$V_N$ which is the difference between the two electrodes is used as input, but FIG. 11B illustrates an example in which signals are output within the input dynamic range via offset correction.

Referring to FIG. 11B, a graph illustrates obtaining a biometric signal upon starting measurement, with the offset initially reduced by Δ (1110) via offset correction so as to prevent such an occasion where it happens to fall within the saturation region over time upon real-time measurement of a biometric signal. Here, blanking region (or blanking period) may refer to a period during which processing for obtaining a biometric signal is not performed on the signal input via the electrode while offset correction is initially performed. As such, when some signals obtained during a certain initial period are disregarded, saturation may not occur as times pass, and only biometric signal may be obtained within the input dynamic range. Thus, it may be possible to obtain a stable biometric signal.

For example, FIG. 11B may illustrate a predicted signal obtained when immediately operating the offset correction circuit when the initial value obtained upon using the result of $V_P$–$V_N$ which is the difference between the two electrodes as an input to the ADC is higher than a predetermined threshold (e.g., Vthreshold). For example, given the case in which the signal first obtained is 0.5V under the assumption that the input dynamic range is ±0.6V, the predetermined threshold (e.g., Vthreshold) is ±0.4V, and DC offset adjustment is performed at, e.g., 1 MΩ×100 nA (100 mV), offset correction may be performed as follows.

In this case, since the signal first obtained exceeds the predetermined threshold (e.g., Vthreshold), offset correction needs to be performed to reduce the same. To that end, offset correction may be performed to reduce the potential at the wrist P electrode or increase the potential at the finger N electrode. Upon determining to perform offset correction to increase the potential at the N electrode, the switch between signal paths may be shorted while the current source is simultaneously operated at, e.g., 25 nA. Thus, since the current of the current source passes through the resistor R (e.g., 100 kΩ) of the low pass filter in 25 nA, an offset of 250 mV occurs at the finger N electrode, leading to Vn. The difference Vp–Vn between the two electrodes may be lowered to be less than 250 mV.

FIG. 11C is a view (1100c) illustrating a signal upon offset correction via adjustment of an intermediate value according to an embodiment.

Referring to FIG. 11C, a graph illustrates obtaining a biometric signal upon starting measurement, with the offset reduced by Δ (1115) via offset correction, in the middle of measurement, so as to prevent such an occasion where it happens to fall within the saturation region over time upon real-time measurement of a biometric signal.

For example, in the case where a severe signal drift occurs, e.g., when such an occasion occurs where a value obtained when the result of $V_P$–$V_N$ is used as an input to the ADC exceeds a predetermined threshold (e.g., Vthreshold) in the middle of biometric signal measurement, the offset correction circuit may be operated to shift the difference Vp−Vn between the two electrodes to fall within the input dynamic range, thereby allowing a stable biometric signal to be obtained.

Figure 12A:
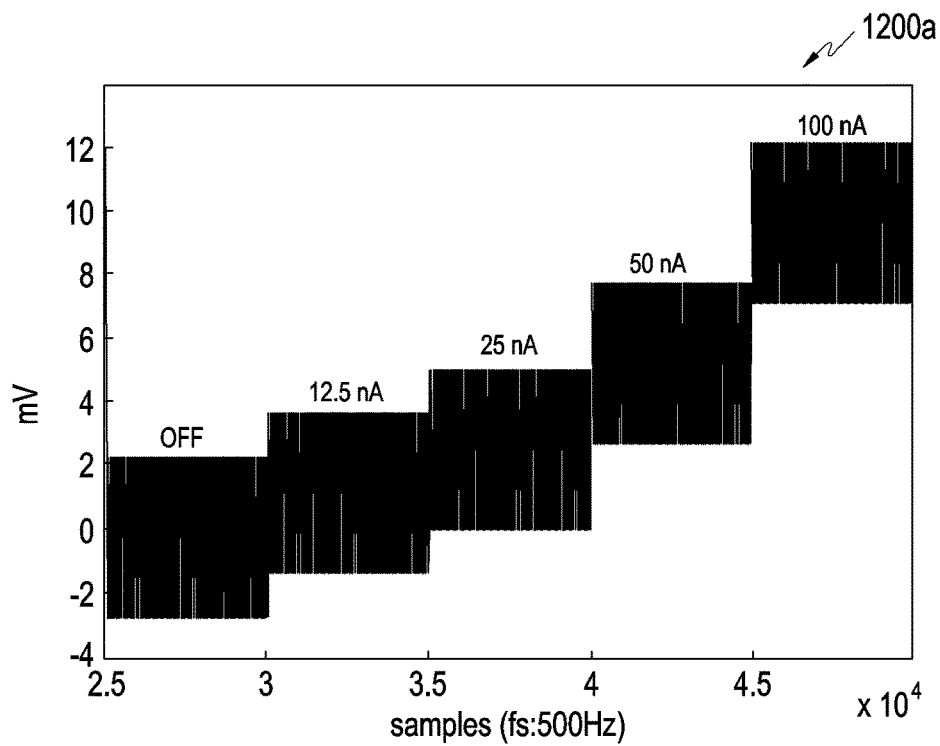
FIG. 12A is a graph illustrating offset being adjusted in a positive direction, in response to a magnitude of current according to an embodiment of the disclosure.

FIG. 12A is a graph 1200a illustrating offset being adjusted in a positive direction, in response to a magnitude of current according to an embodiment of the disclosure.

FIG. 12A illustrates measurement of the DC offset relationship adjusted corresponding to the magnitude of current under the assumption that a sine wave of, e.g., 5 mVpp and 5 hertz (Hz) is used as the input signal, similar to the biometric signal, while a predetermined value (e.g., 51 kΩ) is used as the resistance of the low pass filter LPF in an experimental environment. Here, each of the current sources (e.g., ILEADOFFP and ILEADOFFN) at the first electrode (e.g., INP) and the third electrode (e.g., INN) may be set to correspond to a sink or a source.

Referring to FIG. 12A, the horizontal axis may denote the time axis, and the vertical axis may denote the difference between the potential (e.g., Vp) at the first electrode and the potential (e.g., Vn) at the third electrode. For example, when a signal in the form of a sine wave of 5 Hz is input as an input signal similar to the biometric signal, if the output signal sampled in the time units of 500 Hz on the time axis is measured, the graph of FIG. 12A may be obtained.

For example, corresponding to the current magnitudes of 12.5 nA, 25 nA, 50 nA, and 100 nA, the DC offset due to the potential difference between the potential at the first electrode and the potential at the third electrode may be adjusted to 0.637 mV, 1.27 mV, 2.5 mV, and 5 mV in the positive direction. When the first electrode (e.g., INP) is set as a source, and the third electrode (e.g., INN) is set as a sink under the above-described experimental environment according to an embodiment of the disclosure, such an experimental result may be obtained that the offset increases in the positive direction corresponding to each current level. Similar to the theoretical results, the experimental results of FIG. 12A reveals that offset is further adjusted in proportion as the current doubles.

Figure 12B:
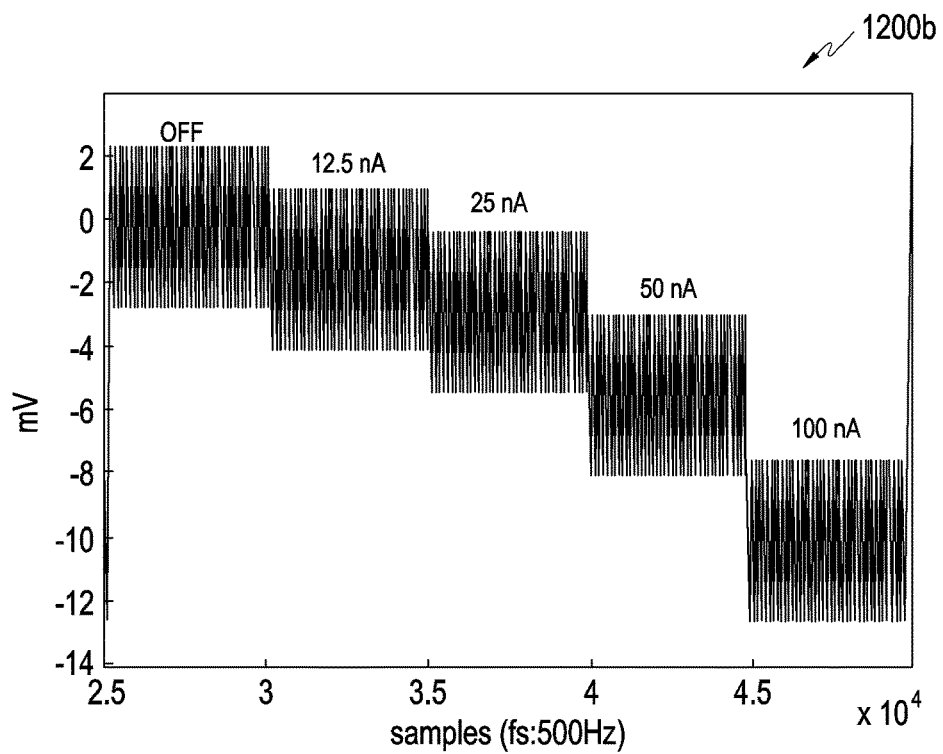
FIG. 12B is a graph illustrating offset being adjusted in a negative direction, in response to a magnitude of current according to an embodiment of the disclosure.

In contrast, FIG. 12B is a graph (1200b) illustrating offset being adjusted in a negative direction, in response to a magnitude of current according to an embodiment of the disclosure.

Referring to FIG. 12B, when the first electrode (e.g., INP) is set as a sink, and the third electrode (e.g., INN) is used as a source under the assumption that, e.g., a sine wave of 5 mVpp and 5 Hz is used which is similar to the biometric signal while using a predetermined value (e.g., 51 kΩ) as the resistance of the low pass filter (LPF) in an experimental environment similarly to FIG. 12A, as shown in FIG. 12B, the result of the experiment may reveal that the offset increases in the negative direction, i.e., the offset reduces.

According to the graphs of FIGS. 12A and 12B, it may be identified that as the current increases at a larger width, the DC offset may be further adjusted in the positive direction or negative direction.

Figure 13:
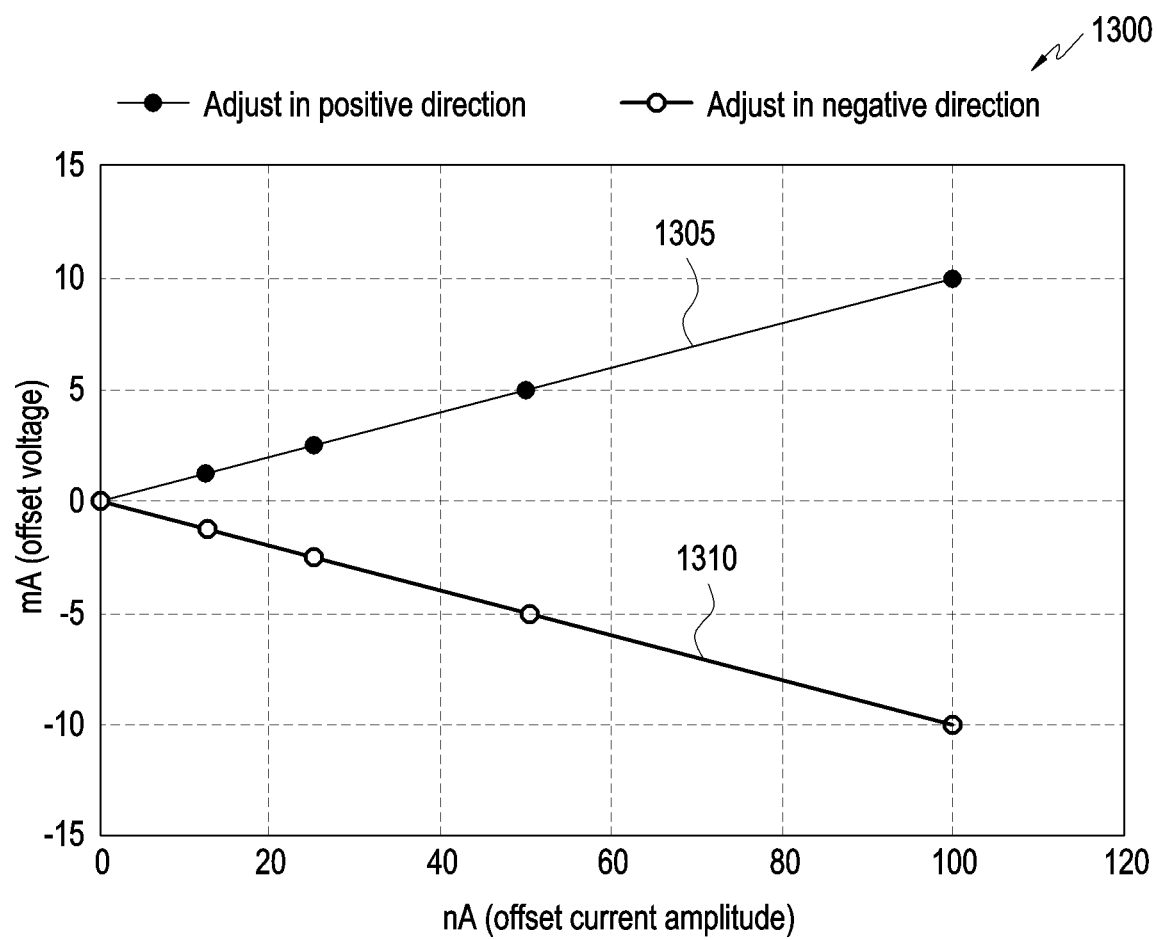
FIG. 13 is a graph illustrating a relationship between current and offset linearly varied according to a magnitude of current, according to an embodiment of the disclosure.

The offset varied according to the magnitude of current may be shown in graph, as shown in FIG. 13.

FIG. 13 is a graph (1300) illustrating a relationship between current and offset linearly varied according to a magnitude of current according to an embodiment of the disclosure.

Referring to FIG. 13, as the magnitude of current increases, the offset is varied linearly in proportion. When the first electrode (e.g., INP) is set as a sink, and the third electrode (e.g., INN) is set as a source, the offset increases in proportion (or the offset reduces in proportion), in the negative direction 1310 corresponding to the width at which the current magnitude increases. When the first electrode (e.g., INP) is set as a source, and the third electrode (e.g., INN) is set as a sink, the offset may increase in proportion in the positive direction 1305, corresponding to the width at which the current magnitude increases.

As described above, it may be identified that the resistance capability of DC offset may be varied depending on the resistance of the low pass filter (LPF). Here, since the resistance of the low pass filter (LPF) is a fixed value, the DC offset may be adjusted by changing the resistance. Thus, when a higher resistance is used, the offset may be adjusted in a wider range. For example, when 1 MΩ is used as the resistance R of the low pass filter (LPF), 1 nF may be used as the capacitance C of the low pass filter (LPF) for the same cutoff frequency. For example, in such a case, the respective offsets of the first electrode (e.g., INP) and the third electrode (e.g., INN) may be adjusted by 12.5 mV, 25 mV, 50 mV, and 100 mV, corresponding to the current magnitudes of 12.5 nA, 25 nA, 50 nA, and 100 nA, and when adjustment is performed using both the first electrode (e.g., INP) and the third electrode (e.g., INN), offset adjustment of up to 200 mV may be performed.

Figure 14:
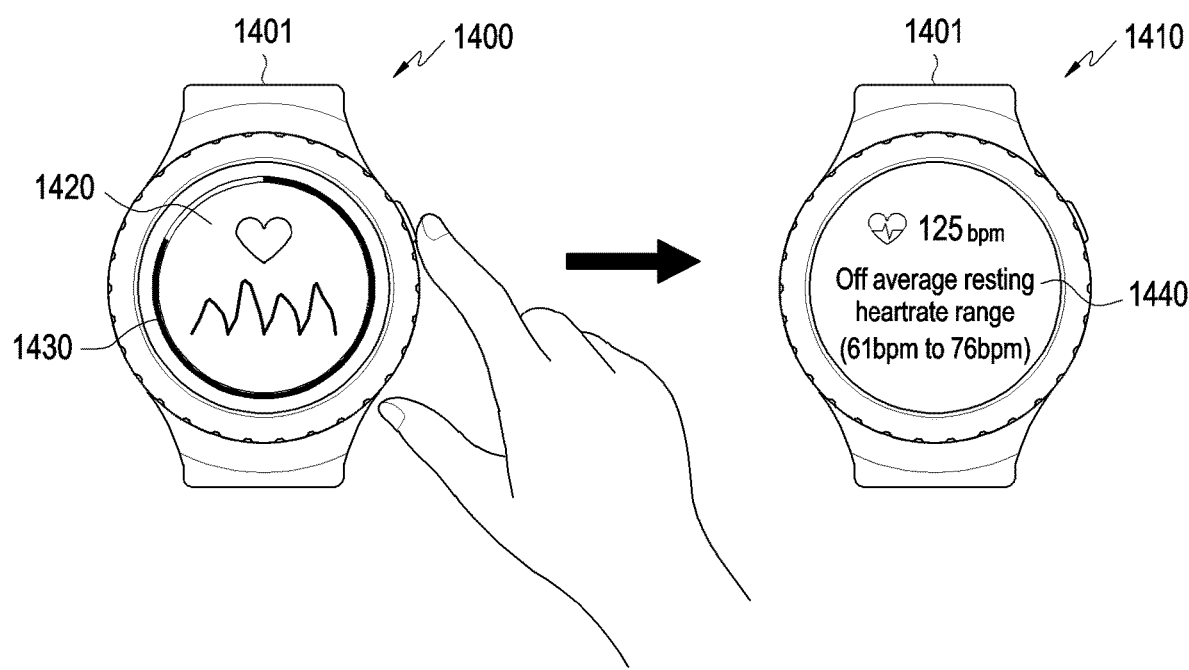
FIG. 14 is a view illustrating a user interface from which notification information is output upon measuring a biometric signal in a wearable electronic device, according to an embodiment of the disclosure.

FIG. 14 is a view (1400) illustrating a user interface from which notification information is output upon measuring a biometric signal in a wearable electronic device, according to an embodiment of the disclosure.

Referring to FIG. 14, a wearable electronic device 1401 (e.g., the electronic device 101 of FIG. 1 or the biometric signal processing device 301 of FIG. 3) may continuously or periodically measure the user's biometric signal. The wearable electronic device 1401 may display, on the display 1420 of the wearable electronic device 1401, a user interface 1420 based on the biometric signal measured upon executing an application for biometric signal measurement (e.g., an ECG application or a health-care application).

According to an embodiment of the disclosure, the wearable electronic device 1401 may provide an ECG function and a heartbeat notification function. For example, the ECG function may be the function of checking the user's heartbeat for a predetermined time, and the heartbeat function may be the function of checking the irregular heartbeat, as diagnosed in the ECG.

For example, ECG measurement may be started while the user stays still or stands for a designated time, e.g., 30 seconds, with the user's finger placed on one side surface of the wearable electronic device 1401 worn on the user's wrist (1400). In this case, to inform the user that measurement is being performed, measurement-related information, such as measurement progress, measurement time, and waveform upon measurement, may be provided on the display 1420 of the wearable electronic device 1401, using visual elements 1430, e.g., graphical objects. For example, the measurement context may be indicated using a way of display in which at least one of the edge light color or edge light flickering of the display 1420 of the electronic device 1401 is varied.

According to an embodiment of the disclosure, the wearable electronic device 1401 may output the results of output based on the biometric signal measured (1410). When the measured biometric signal is higher or lower than the value measured ordinarily based on the measured biometric signal, alert information 1440 may be output to allow the user to recognize the same. Further, various methods, such as using an alert sound and a graphical object or displaying a guide for recommending a precise diagnosis, may be used to allow the user to intuitively know health abnormality in relation to irregular heartbeat. Further, an alert may be output in various manners for various abnormal measurement contexts other than the user-related abnormality as in the case where the part of the electrode contacting the user's body portion peels off the wearable electronic device 1401 upon a self-checkup.

The electronic device according to various embodiments may be one of various types of electronic devices. The electronic devices may include, for example, a portable communication device (e.g., a smart phone), a computer device, a portable multimedia device, a portable medical device, a camera, a wearable device, or a home appliance. According to an embodiment of the disclosure, the electronic devices are not limited to those described above.

It should be appreciated that various embodiments of the disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment of the disclosure, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment of the disclosure, a method according to various embodiments of the disclosure may be included and provided in a computer program product. The computer program products may be traded as commodities between sellers and buyers. The computer program product may be distributed in the form of a machine-readable storage medium (e.g., compact disc read only memory (CD-ROM)), or be distributed (e.g., downloaded or uploaded) online via an application store (e.g., Play Store™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments of the disclosure, each component (e.g., a module or a program) of the above-described components may include a single entity or multiple entities. According to various embodiments of the disclosure, one or more of the above-described components may be omitted, or one or more other components may be added. Alternatively or additionally, a plurality of components (e.g., modules or programs) may be integrated into a single component. In such a case, according to various embodiments of the disclosure, the integrated component may still perform one or more functions of each of the plurality of components in the same or similar manner as they are performed by a corresponding one of the plurality of components before the integration. According to various embodiments of the disclosure, operations performed by the module, the program, or another component may be carried out sequentially, in parallel, repeatedly, or heuristically, or one or more of the operations may be executed in a different order or omitted, or one or more other operations may be added.

According to an embodiment of the disclosure, there is provided a storage medium storing instructions, the instructions configured to be executed by at least one processor to enable the at least one processor to perform at least one operation, the at least one operation comprising measuring an offset between voltages via at least two electrodes among a plurality of electrodes for measuring a biometric signal in a wearable electronic device and correcting the offset to allow the measured offset to fall within a threshold range.

As is apparent from the foregoing description, according to various embodiments of the disclosure, even when a contact impedance for a biometric signal is not uniformly input due to problems with various measurement environments when measuring the biometric signal, it is possible to allow the contact impedance to be stably input within a constant range by correcting the same. Thus, it is possible to more stably obtain a biometric signal.

According to various embodiments of the disclosure, it is possible to prevent deterioration of performance, in measurement of a biometric signal, due to a change in contact impedance that occurs while wearing a wearable electronic device.

According to various embodiments of the disclosure, it is possible to adjust the contact impedance to fall within a threshold range although the contact impedance is varied by various factors, such as the wearing condition and measurement environment of the wearable electronic device. Thus, diversified electrode materials may be used for wearable electronic devices, and the design development range of wearable electronic devices may be expanded.

While the disclosure has been shown and described with reference to various embodiments thereof, it will be understood by those skilled in the art that various changes in form and details may be made therein without departing from the spirit and scope of the disclosure as defined by the appended claims and their equivalents.

What is claimed is:

1. A wearable electronic device comprising:
a display;
a plurality of electrodes configured to measure a biometric signal, wherein a first electrode and a second electrode among the plurality of electrodes disposed on a first surface of the wearable electronic device are configured to contact a first part of a living body, and a third electrode disposed on a second surface of the wearable electronic device is configured to contact a second part of the living body;
an offset correction circuit;
at least one processor operatively connected with the plurality of electrodes and the offset correction circuit; and
a memory operatively connected with the at least one processor,
wherein the memory stores instructions executed to enable the at least one processor to:
measure an offset between a first voltage via the first electrode and a second voltage via the third electrode, with respect to a reference voltage, as the reference voltage is applied via the second electrode among the plurality of electrodes while the wearable electronic device is worn on a user's wrist,
correct the offset via the offset correction circuit to allow the measured offset to fall within a threshold range, and
display a user interface based on the biometric signal measured upon executing an application for biometric signal measurement.

2. The wearable electronic device of claim 1, wherein the offset correction circuit includes:
a first current source between an output terminal of the first electrode and an input terminal of a differential amplifier; and
a second current source between an output terminal of the third electrode and an input terminal of the differential amplifier.

3. The wearable electronic device of claim 2, wherein the instructions further enable the at least one processor to:
measure the offset between the first voltage output from the first electrode and the second voltage output from the third electrode using the differential amplifier, and
when the measured offset falls out of the threshold range, correct the offset by adjusting a current magnitude of any one of the first current source or the second current source for a voltage for the first electrode and a voltage for the third electrode.

4. The wearable electronic device of claim 1, wherein the offset correction circuit includes:
a first low pass filter receiving the first voltage output from the first electrode via a buffer;
a second low pass filter receiving the second voltage output from the third electrode via a buffer;
a first current source between an output terminal of the first low pass filter and an input terminal of a differential amplifier; and
a second current source between an output terminal of the second low pass filter and the input terminal of the differential amplifier.

5. The wearable electronic device of claim 4, wherein the instructions further enable the at least one processor to:
measure the offset between the first voltage and the second voltage using the differential amplifier, and
when the measured offset falls out of the threshold range, correct the offset via the offset correction circuit.

6. The wearable electronic device of claim 5, wherein the instructions further enable the at least one processor to, when the measured offset falls out of the threshold range, correct the offset by adjusting a current magnitude of any one of the first current source or the second current source for a voltage for the first electrode and a voltage for the third electrode.

7. The wearable electronic device of claim 6, wherein the instructions further enable the at least one processor to, when the measured offset is larger than an upper limit threshold of the threshold range, apply a second current of the second current source in a direction towards the third electrode to increase the voltage for the third electrode and decrease the voltage for the first electrode.

8. The wearable electronic device of claim 7, wherein a voltage applied to the input terminal of the differential amplifier is a sum of the voltage for the third electrode and a voltage resultant from multiplying a resistance of the second low pass filter by the second current of the second current source.

9. The wearable electronic device of claim 8, wherein the instructions further enable the at least one processor to adjust the offset to a magnitude corresponding to the voltage resultant from multiplying the resistance of the second low pass filter by the second current of the second current source.

10. The wearable electronic device of claim 6, wherein the instructions further enable the at least one processor to, when the measured offset is smaller than a lower limit threshold of the threshold range, apply a first current of the first current source in a direction towards the first electrode to decrease the voltage for the third electrode and increase the voltage for the first electrode.

11. The wearable electronic device of claim 10, wherein a voltage applied to the input terminal of the differential amplifier is a sum of the voltage for the first electrode and a voltage resultant from multiplying a resistance of the first low pass filter by the first current of the first current source.

12. The wearable electronic device of claim 11, wherein the instructions further enable the at least one processor to adjust the offset to a magnitude corresponding to the voltage resultant from multiplying the resistance of the first low pass filter by the first current of the first current source.

13. A method for processing a biometric signal in a wearable electronic device, the method comprising:
measuring an offset between a first voltage via a first electrode and a second voltage via a third electrode, with respect to a reference voltage, as the reference voltage is applied via a second electrode among a plurality of electrodes for measuring the biometric signal in the wearable electronic device, wherein the first electrode and the second electrode among the plurality of electrodes disposed on a first surface of the wearable electronic device are configured to contact a first part of a living body, and the third electrode disposed on a second surface of the wearable electronic device is configured to contact a second part of the living body;

correcting the offset via an offset correction circuit to allow the measured offset to fall within a threshold range; and displaying, on a display of the wearable electronic device, a user interface based on the biometric signal measured upon executing an application for biometric signal measurement.

14. The method of claim 13, wherein the correcting of the offset includes, when the measured offset falls out of the threshold range, correcting the offset by adjusting a current magnitude of any one of a first current source, between an output terminal of the first electrode and an input terminal of the differential amplifier, or a second current source, between an output terminal of the third electrode and an input terminal of the differential amplifier, for a voltage for the first electrode and a voltage for the third electrode.

15. The method of claim 14, further comprising, when the measured offset is larger than an upper limit threshold of the threshold range, correcting the offset by applying a second current of the second current source in a direction towards the third electrode to increase the voltage for the third electrode and decrease the voltage for the first electrode.

16. The method of claim 14, further comprising, when the measured offset is smaller than a lower limit threshold of the threshold range, correcting the offset by applying a first current of the first current source in a direction towards the first electrode to decrease the voltage for the third electrode and increase the voltage for the first electrode.

17. The method of claim 16, further comprising:

receiving, by a first low pass filter included in the offset correction circuit, the first voltage output from the first electrode via a buffer; and receiving, by a second low pass filter included in the offset correction circuit, the second voltage output from the third electrode via a buffer, wherein a voltage applied to the input terminal of the differential amplifier is a sum of the voltage for the first electrode and a voltage resultant from multiplying a resistance of the first low pass filter by the first current of the first current source.

18. The method of claim 17, wherein the correcting of the offset includes adjusting the offset to a magnitude corresponding to the voltage resultant from multiplying the resistance of the second low pass filter by the second current of the second current source.

* * * * *